US008882765B2

(12) United States Patent
Kassab et al.

(10) Patent No.: US 8,882,765 B2
(45) **Date of Patent: *Nov. 11, 2014**

(54) DEVICES, SYSTEMS, AND METHODS FOR EPICARDIAL NAVIGATION

(71) Applicant: CVDevices, LLC, San Diego, CA (US)

(72) Inventors: Ghassan S. Kassab, La Jolla, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/759,579

(22) Filed: Feb. 5, 2013

(65) Prior Publication Data

US 2013/0218156 A1 Aug. 22, 2013

Related U.S. Application Data

(63) Continuation of application No. 12/521,642, filed as application No. PCT/US2008/000834 on Jan. 23, 2008, now Pat. No. 8,366,707.

(51) Int. Cl.

| | |
|---|---|
| ***A61B 18/14*** | (2006.01) |
| *A61B 18/00* | (2006.01) |
| *A61B 17/30* | (2006.01) |
| *A61B 19/00* | (2006.01) |
| *A61B 17/34* | (2006.01) |
| *A61B 17/00* | (2006.01) |

(52) U.S. Cl.

CPC ... *A61B 18/1492* (2013.01); *A61B 2018/00392* (2013.01); *A61B 2017/308* (2013.01); *A61B 2018/00375* (2013.01); *A61B 2018/00839* (2013.01); *A61B 2019/2253* (2013.01); *A61B 17/3478* (2013.01); *A61B 2018/00291* (2013.01); *A61B 2017/00243* (2013.01); *A61B 2017/00247* (2013.01)

USPC ............ 606/41

(58) Field of Classification Search

USPC ............ 606/22–31, 41–50; 607/122; 600/424

See application file for complete search history.

(56) References Cited

U.S. PATENT DOCUMENTS

| | | | |
|---|---|---|---|
| 3,674,014 | A | 7/1972 | Tillander |
| 5,161,540 | A | 11/1992 | Mueller |
| 5,429,131 | A | 7/1995 | Scheinman et al. |

(Continued)

FOREIGN PATENT DOCUMENTS

| | | |
|---|---|---|
| WO | WO 2008/005388 | 1/2008 |
| WO | WO 2008/010905 | 1/2008 |

OTHER PUBLICATIONS

PCT/US2008/000834, PCT Search Report and Written Opinion, dated Jul. 18, 2008.

*Primary Examiner* — Michael Peffley

*Assistant Examiner* — Khadijeh Vahdat

(74) *Attorney, Agent, or Firm* — Reichel IP LLP; Mark C. Reichel; Natalie J. Dean

(57) ABSTRACT

Devices, systems, and methods for epicardial navigation. In at least one exemplary embodiment of a system for navigating an elongated body on a surface of a tissue of the present disclosure, the system comprises (a) an internal elongated body comprising a distal end and a first element positioned at or near the distal end of the internal elongated body, the internal elongated body devoid of an ablation contact, and (b) an external elongated body comprising a distal end and a second element and an ablation contact positioned at or near the distal end of the external elongated body, the ablation contact being configured to remove or destroy tissue.

20 Claims, 21 Drawing Sheets

(56) References Cited

U.S. PATENT DOCUMENTS

| | | | |
|---|---|---|---|
| 5,843,153 | A | 12/1998 | Johnston et al. |
| 6,292,678 | B1 | 9/2001 | Hall et al. |
| 6,332,089 | B1 | 12/2001 | Acker et al. |
| 6,385,472 | B1 | 5/2002 | Hall et al. |
| 6,662,034 | B2 | 12/2003 | Segner et al. |
| 6,699,240 | B2 | 3/2004 | Francischelli |
| 6,807,968 | B2 | 10/2004 | Francischelli et al. |
| 6,980,843 | B2 | 12/2005 | Eng et al. |
| 7,001,415 | B2 | 2/2006 | Hooven |
| 7,008,418 | B2 | 3/2006 | Hall et al. |
| 7,094,235 | B2 | 8/2006 | Francischelli |
| 7,211,082 | B2 | 5/2007 | Hall et al |
| 7,250,051 | B2 | 7/2007 | Francischelli |
| 8,048,072 | B2 | 11/2011 | Verin et al. |
| 2001/0007070 | A1 | 7/2001 | Stewart et al. |
| 2002/0072662 | A1 | 6/2002 | Hall et al. |
| 2002/0128639 | A1 | 9/2002 | Pless et al. |
| 2004/0034347 | A1 | 2/2004 | Hall et al. |
| 2004/0143260 | A1 | 7/2004 | Francischelli |
| 2004/0230131 | A1 | 11/2004 | Kassab et al. |
| 2005/0033280 | A1 | 2/2005 | Francischelli et al. |
| 2005/0187545 | A1 | 8/2005 | Hooven et al. |
| 2006/0009759 | A1 | 1/2006 | Christian et al. |
| 2006/0116633 | A1 | 6/2006 | Shachar |
| 2006/0200119 | A1 | 9/2006 | Vaska et al. |
| 2008/0015670 | A1 | 1/2008 | Pappone |

400
405
410
415
420

425
430
435
440
445

450
460
470
480
490
500 envelope data, peak-peak, of voltage at the detection electrodes envelope data, peak-peak, of voltage at the detection electrodes

DEVICES, SYSTEMS, AND METHODS FOR EPICARDIAL NAVIGATION

PRIORITY

The present U.S. continuation application is related to, and claims the priority benefit of, U.S. Nonprovisional patent application Ser. No. 12/521,642, filed on Jun. 29, 2009 and issued as U.S. Pat. No. 8,366,707 on Feb. 5, 2013, which is related to, claims the priority benefit of, and is a U.S. national stage patent application of, International Patent Application Serial No. PCT/US2008/000834, filed Jan. 23, 2008, which (1) claims priority to, and in at least some designated countries should be considered a continuation-in-part application of, International Patent Application Serial No. PCT/US2007/015239, filed on Jun. 29, 2007, (2) claims priority to, and in at least some designated countries should be considered a continuation-in-part application of, International Patent Application Serial No. PCT/US2007/015207, filed on Jun. 29, 2007, and (3) claims priority to U.S. Provisional Patent Application Ser. No. 60/881,839, filed on Jan. 23, 2007. The contents of each of the aforementioned patent applications and patents are hereby incorporated by reference in their entirety into this disclosure.

BACKGROUND

Atrial fibrillation ("AF") of the human heart is a common arrhythmia affecting millions of people worldwide. Underlying causes include dysfunction of the sinus node, coronary artery disease, and pericarditis. Theoretically, the AF mechanism involves two main processes: (1) higher automaticity in one or more rapidly depolarizing foci and (2) reentry of conduction involving one or more circuits. Rapid atrial foci, often located in at least one of the superior pulmonary veins, can begin AF in predisposed patients. In addition, the "multiple-wavelet hypothesis" has been proposed as a potential mechanism for AF caused by conduction reentry. According to the hypothesis, normal conduction wave fronts break up, resulting in a number of self-perpetuating "daughter" wavelets that spread through the atria causing abnormal contraction of the myocardium.

Surgical treatment of AF requires the construction of barriers to conduction within the right atrium and left atrium to restrict the amount of myocardium available to spread reentrant wave fronts, thereby inhibiting sustained AF. By making incisions in the myocardium, conduction is interrupted. Since it has been demonstrated that the pulmonary veins often contain the specific rapidly-depolarizing loci, incisions encircling the pulmonary veins can help prevent AF. Similarly, potentially arrhythmogenic foci close to the pulmonary veins, as well as specific atrial regions with the shortest refractory periods, may be isolated from the rest of the atria by strategically placed incisions. Although the risk of such surgery alone is typically less than 1%, the need for median sternotomy and the use of cardiopulmonary bypass, as well as a risk of short-term fluid retention, make this procedure less than ideal.

As an alternative to surgery, catheter ablation has evolved as a standard therapy for patients at high risk for ventricular and supraventricular tachyarrhythmia. The recognition that foci triggering AF frequently initiate within the pulmonary veins has led to ablation strategies that target this zone or that electrically isolate the pulmonary veins from the left atrium. In the superior vena cava, the right atrium, left atrium, and coronary sinus were found as other sites of arrhythmogenic foci.

In most circumstances, the cardiac ablation catheter is inserted into a blood vessel (artery or vein), usually through an entry site located in the upper leg or neck. Under fluoroscopy, the tube is navigated through the blood vessels until it reaches the heart. In the heart, electrodes at the catheter tip gather data that pinpoint the location of faulty tissue in the heart (electrical mapping). Once the site is identified, the device delivers either radiofrequency energy (RF ablation) or intense cold (cryoablation) to destroy the small section of tissue. The major goal of this procedure is segmental pulmonary vein isolation and circumferential pulmonary vein ablation. The circumferential ablation strategy yields either an atriovenous electrical disconnection, as demonstrated by elimination of pulmonary vein ostial potentials and absence of discrete electrical activity inside the lesion during pacing from outside the ablation line, or a profound atrial electroanatomical remodeling as expressed by voltage abatement inside and around the encircled areas involving to some extent the posterior wall of the left atrium. The endpoint is the electrical isolation of the pulmonary veins from the left atrium, as they house foci triggering AF in about 80% to about 95% of cases and seem to play a key role in arrhythmia maintenance.

Possible complications of catheter ablation for AF include systemic embolism, pulmonary vein stenosis, pericardial effusion, cardiac tamponade, and phrenic nerve paralysis. The majority of these risks stem from the ablation of an incorrect region. Hence, proper navigation during cardiac ablation is one of the greatest challenges for the electrophysiologist performing the procedure.

BRIEF SUMMARY

Disclosed herein are systems and methods for navigating a catheter along a tissue surface, such as the epicardial surface of the heart. The disclosed embodiments include, but are not limited to, systems and methods useful for epicardial ablation. Various embodiments permit ablation of the epicardial surface of the heart using an external ablation catheter in the pericardial space and an internal guide catheter within the heart. Such a configuration allows the clinician to precisely target for ablation specific locations on the cardiac tissue.

At least some embodiments include a system for navigating a catheter on a surface of a tissue, comprising an external catheter having a distal end and a first magnet positioned at or near the distal end of the external catheter; and an internal catheter comprising a distal end and a first magnet positioned at or near the distal end of the internal catheter; wherein the internal catheter is configured for engaging the external catheter when a portion of the external catheter is positioned on or adjacent to a first surface of the tissue and a portion of the internal catheter is positioned on or adjacent to an opposing surface of the tissue, such that manipulation of the internal catheter is capable of directing the external catheter. In at least some embodiments, the first surface of the tissue comprises an epicardial surface of a heart, and the opposing surface of the tissue comprises an endocardial surface of the heart.

In some embodiments, the external catheter further comprises an ablation contact positioned at or near the distal end of the external surface, the ablation contact being configured to remove or destroy tissue.

The first magnet of the internal catheter may comprise a first electrode capable of transitioning between a magnetized state, in which the electrode attracts the first magnet of the external catheter, and a nonmagnetized state, in which the electrode does not significantly attract the first magnet of the external catheter. The internal catheter may further comprise a second electrode positioned at or near the distal end of the internal catheter, the second electrode of the internal catheter being capable of transitioning between a magnetized state, in which the electrode attracts the first magnet of the external catheter, and a nonmagnetized state, in which the electrode does not significantly attract the first magnet of the external catheter.

Some embodiments of internal catheter may further comprise a pair of excitation electrodes positioned at or near the distal end of the internal catheter and a pair of detection electrodes positioned on the internal catheter between the pair of the excitation electrodes. A proximal end of each of the pair of excitation electrodes and each of the pair of detection electrodes may be connected to a processor, the processor being capable of collecting conductance data. The conductance data may be determined at each of a plurality of locations. The processor may also be capable of determining a profile of a body lumen using the conductance data.

In at least some embodiments, the conductance data comprises a first conductance value determined at each of the plurality of locations when the excitation electrodes and detection electrodes are immersed in a first fluid with a first conductivity and a second conductance value determined at each of the plurality of locations when the excitation electrodes and detection electrodes are immersed in a second fluid with a second conductivity. The first conductivity may not equal the second conductivity.

In some embodiments, the internal catheter further comprises a third electrode and a fourth electrode, each of which is positioned at or near the distal end of the internal catheter and each of which is capable of transitioning between a magnetized state, in which the electrode attracts the first magnet of the external catheter, and a nonmagnetized state, in which the electrode does not significantly attract the first magnet of the external catheter. The internal catheter may be capable of forming a loop within the heart such that the first, second, third, and fourth electrodes are located within the heart. The internal catheter may further comprise a passageway for passing a fluid through the internal catheter to the body lumen.

In some embodiments, the first magnet of the external catheter comprises a first electrode capable of transitioning between a magnetized state, in which the electrode attracts the first magnet of the internal catheter, and a nonmagnetized state, in which the electrode does not significantly attract the first magnet of the internal catheter. The external catheter may further comprise a second magnet positioned at or near the distal end of the external catheter, including a second electrode being capable of transitioning between a magnetized state, in which the electrode attracts the first magnet of the internal catheter, and a nonmagnetized state, in which the electrode does not significantly attract the first magnet of the internal catheter.

Also disclosed herein are embodiments of systems for use with a vacuum source for ablating a tissue of a heart, comprising an engagement catheter comprising a proximal end, a distal end, and first and second lumens extending between the proximal end and the distal end; an external catheter comprising a distal end, an ablation contact positioned at or near the distal end of the external catheter, and a first magnet positioned at or near the distal end of the external catheter, wherein the external catheter is configured such that the external catheter is capable of at least partial insertion into the second lumen of the engagement catheter; an internal catheter comprising a distal end and a first magnet positioned at or near the distal end of the internal catheter; and a vacuum port located at the proximal end of the engagement catheter, the vacuum port being operatively connected to the first lumen of the engagement catheter and capable of operative connection to the vacuum source; wherein the first lumen of the engagement catheter includes a suction port located at or near the distal end of the engagement catheter, the suction port being configured to removably attach to a targeted tissue on the interior of a wall of the heart, such that the suction port is capable of forming a reversible seal with the targeted tissue when the vacuum source is operatively attached to the vacuum port, wherein the internal catheter is configured for engaging the external catheter when a portion of the external catheter is positioned on or adjacent to an epicardial surface of the heart and a portion of the internal catheter is positioned on or adjacent to an endocardial surface of the heart, such that manipulation of the internal catheter is capable of directing the external catheter, and wherein the system is capable of enlarging a pericardial space between the targeted tissue and a pericardial sac that surrounds the heart by retracting the targeted tissue away from the pericardial sac.

In various embodiments, the internal catheter further comprises a pair of excitation electrodes positioned at or near the distal end of the internal catheter and a pair of detection electrodes positioned on the internal catheter between the pair of the excitation electrodes. A proximal end of each of the pair of excitation electrodes and each of the pair of detection electrodes may be connected to a processor, the processor being capable of collecting conductance data. The conductance data may comprise a first conductance value determined at each of a plurality of locations when the excitation electrodes and detection electrodes are immersed in a first fluid with a first conductivity and a second conductance value determined at each of the plurality of locations when the excitation electrodes and detection electrodes are immersed in a second fluid with a second conductivity. In at least some embodiments, the first conductivity does not equal the second conductivity.

Also disclosed herein are methods of navigation and ablation. In some embodiments, a method of ablating a tissue comprises providing an external catheter comprising a distal end, a first magnet positioned at or near the distal end of the external catheter, and an ablation contact positioned at or near the distal end of the external catheter, the ablation contact being configured to remove or destroy tissue; providing an internal catheter comprising a distal end and a first magnet positioned at or near the distal end of the internal catheter, the internal catheter being configured for engaging the external catheter; placing the distal end of the external catheter adjacent to a first surface of the tissue; placing the distal end of the internal catheter adjacent to an opposing surface of the tissue; manipulating the internal catheter to direct the ablation contact of the external catheter to contact a first targeted location on the first surface of the tissue; and ablating the first targeted location on the first surface of the tissue. In at least some embodiments, the tissue may comprise cardiac tissue, the first surface of the tissue may comprise the epicardial surface of the cardiac tissue, and the opposing surface of the tissue may comprise the endocardial surface of the cardiac tissue.

In some embodiments, the step of manipulating the internal catheter to direct the ablation contact of the external catheter to contact a first targeted location on the first surface of the tissue comprises (i) engaging the first magnet of the external catheter with the first magnet of the internal catheter such that moving the first magnet of the internal catheter moves the first magnet of the external catheter, (ii) moving the first magnet of the internal catheter along the endocardial surface of the cardiac tissue such that the ablation contact of the external catheter moves along the epicardial surface of the cardiac tissue to the first targeted location on the epicardial surface of the cardiac tissue.

In some embodiments, the step of manipulating the internal catheter to direct the ablation contact of the external catheter to contact a first targeted location on the first surface of the tissue may comprise (i) positioning the first electrode of the internal catheter, (ii) switching the first electrode of the internal catheter to the magnetized state such that the ablation contact of the external catheter is moved to the first targeted location on the first surface of the tissue.

In at least some embodiments, the methods further comprise the steps of manipulating the internal catheter to direct the ablation contact of the external catheter to contact a second targeted location on the first surface of the tissue and ablating the second targeted location on the first surface of the tissue.

The step of manipulating the internal catheter to direct the ablation contact of the external catheter to contact a second targeted location on the first surface of the tissue may further comprise (i) switching the first electrode of the internal catheter to the nonmagnetized state, and (ii) switching the second electrode of the internal catheter to the magnetized state such that the ablation contact of the external catheter is moved to the second targeted location on the first surface of the tissue.

In some embodiments, the method further includes ablating the first surface of the tissue between the first targeted location on the first surface of the tissue and the second targeted location on the first surface of the tissue. Moreover, some embodiments include ablating the first surface of the tissue in a specified circumference, the circumference being approximately defined by a loop of the internal catheter.

The step of manipulating the internal catheter to direct the ablation contact of the external catheter to contact a first targeted location on the first surface of the tissue may further comprise (i) measuring a first conductance value at a first location, (ii) measuring a second conductance value at a second location, and (iii) determining a profile of a body lumen based on the first conductance value and the second conductance value.

In at least some embodiments, a method of ablating a targeted tissue on an epicardial surface of a heart may comprise providing an external catheter comprising a distal end, a first magnet positioned at or near the distal end of the external catheter, and an ablation contact positioned at or near the distal end of the external catheter, wherein the ablation contact is configured to remove or destroy tissue; providing an internal catheter comprising a distal end, a first electrode positioned at or near the distal end of the internal catheter, and a second electrode positioned at or near the distal end of the internal catheter; placing the distal end of the internal catheter within the heart, such that the first and second electrodes are positioned within the heart at a desired ablation location and in a desired ablation pattern; activating the first electrode of the internal catheter such that the ablation contact of the external catheter is directed to the targeted tissue at a first location; activating the ablation contact to ablate the targeted tissue; deactivating the first electrode of the internal catheter; and activating the second electrode of the internal catheter such that the ablation contact of the external catheter is directed to the targeted tissue at a second location; wherein the targeted tissue is ablated by the ablation contact between the first location and the second location.

Various embodiments further include the steps of extending into a blood vessel an elongated tube having a proximal end, a distal end, and a first lumen, such that the distal end of the tube is in contact with a targeted tissue on the interior of a wall of the heart; aspirating the targeted tissue on the interior of the wall of the heart such that the wall of the heart is retracted away from a pericardial sac surrounding the heart to enlarge a pericardial space between the pericardial sac and the wall of the heart; accessing the pericardial space through the targeted tissue; and inserting at least the distal end of the external catheter into the pericardial space.

Certain embodiments also include the steps of introducing an impedance catheter into the heart; measuring a first conductance value at a first location in the body; and measuring a second conductance value at a second location in the body. At least some embodiments further comprise the step of determining a profile of a body lumen using the conductance data.

DETAILED DESCRIPTION

Figure 1:
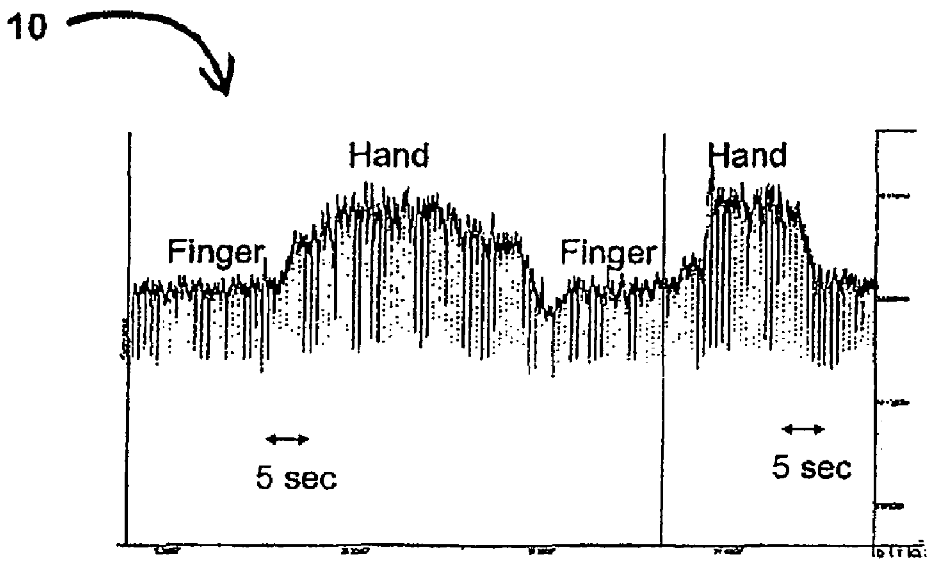
FIG. 1 shows the visual output of an embodiment of a catheter system for localization during an experiment of movement through an interior of a surgical glove.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The disclosed embodiments include, but are not limited to, systems and methods useful for epicardial ablation. For example, various embodiments disclosed herein permit ablation of the epicardial surface of the heart using an external ablation catheter in the pericardial space and an internal guide catheter within the heart. Such a configuration allows the clinician to precisely target for ablation specific locations on the cardiac tissue.

Ablation of the epicardial surface of the cardiac tissue is advantageous because it requires less penetration of tissue destruction than other ablation methods and is therefore useful in preventing transmural damage. This is particularly important for treating ventricular arrhythmias because the ventricular wall is relatively thick. The goal of the ablation is to destroy the arrhythmic cells while preserving the normal cardiac cells, and success is often dependant on the ability to precisely ablate in a specific location.

Proper in vivo localization of catheters, the targeted tissue, and cardiac and venous structure during an ablation or similar medical procedure can therefore be important for the safety and efficacy of the procedure. Localization may be made by using the devices, systems, and methods disclosed in International Patent Application No. PCT/US2007/015239, filed Jun. 29, 2007, the contents of which are incorporated herein by reference. Although localization or visualization during intraluminal catheter navigation by the devices, systems, and methods disclosed herein are advantageous, intraluminal navigation may be performed by any suitable method.

During various medical procedures involving intraluminal insertion of catheters or other devices, proper navigation of the device through body lumens, such as blood vessels or the heart, is critical to the success of the procedure. Indeed, unless the tissue targeted for treatment or diagnosis during the procedure is properly located, the procedure can be ineffective or, even worse, damaging to nearby healthy tissue. Therefore, a number of the embodiments disclosed herein permit a clinician to readily locate a catheter, such as an ablation catheter, or other medical device within a body lumen in relation to body lumen junctions or other anatomical structures within the lumen. This leads to proper localization of targeted tissue and increased favorable outcomes.

Some of the disclosed embodiments measure electrical conductance within the body lumen and display a profile of relative conductance values, while other embodiments use conductance data to calculate luminal cross-sectional areas and display a profile of relative cross-sectional areas along a portion of the lumen. These profiles enable the clinician to readily locate the targeted tissue for further treatment, such as ablation. In some embodiments, the conductance catheter and the ablation catheter is combined into one device so that ablation can occur immediately following localization, without requiring a change of catheters.

Many of the disclosed embodiments do not calculate an absolute value for a lumen's cross-sectional area, but instead measure electrical conductance through a portion of the lumen to form a profile of the lumen. Often, the profile comprises relative conductances taken along the lumen. However, because conductance is proportional to cross-sectional area, as explained herein, the profile can comprise relative cross-sectional areas that have been determined from the conductances taken along the lumen.

By monitoring the profile during catheterization, the clinician can visualize the anatomical structure of the lumen. For example, using a push through or a pull back of a disclosed embodiment of a catheter through a lumen, a clinician is able to localize a junction or other architectural marker in the body lumen. Such a push through or pull back will reflect, in relative terms, the lumen's changes in conductance, and therefore its changes in cross-sectional area, as the catheter moves, thereby depicting changes in lumen structure across a distance. Based on such changes in lumen structure, a clinician can determine the locations of various anatomical markers of the lumen, as well as the location of the catheter in relation to those markers. For example, localization of the junction between the relatively small pulmonary veins and the significantly larger atrium is possible by assessing the change in conductance (and therefore in cross-sectional area) of the lumen as the catheter is pushed through the vein into the atrium.

Once a specific lumen junction or other anatomical structure is localized, the clinician can better treat a targeted tissue at or near that identifying structure. Such treatment may include, for example, ablation, localized drug delivery, angioplasty, or stent delivery. One common use of ablation is to electrically isolate arrhythmogenic foci, which are often found in the superior pulmonary veins, from the left atrium to prevent atrial fibrillation in at-risk patients. To isolate the vein and prevent further arrhythmogenic conduction from the foci, the cardiac tissue surrounding the pulmonary vein at or adjacent to the pulmonary vein-atrial junction is ablated. Ablation can be performed in a number of ways, including mechanically, electrically, using heat, or using cryoablation. Regardless of the method for removing or destroying the targeted tissue, the clinician preparing to ablate an area of cardiac tissue surrounding a pulmonary vein must direct the ablation device, often a catheter configured for ablation, to the targeted tissue surrounding the pulmonary vein-atrial junction.

Various devices, systems, and methods for localization of body lumen junctures disclosed herein permit the clinician to accurately locate the pulmonary vein-atrial junction, as well as confirm the location of the ablation catheter with respect to the junction (and, therefore, the targeted tissue). Indeed, localization using the disclosed embodiments will minimize undesired ablation into the pulmonary veins, which causes shrinkage of collagen and hence pulmonary vein stenosis. It will also minimize the ablation of the atrium too far from the pulmonary vein, where the ablation circumference is too large and isolation of conductance is unlikely.

Experiments have demonstrated the ability of the disclosed embodiments to provide accurate and reliable feedback as to the location of a catheter within a body lumen. For instance, a surgical glove was filled with saline to simulate a left atrium (the palm) and pulmonary veins (the fingers). A catheter configured for localization as described herein was pulled back from inside a finger to the palm, thereby simulating the transition from a pulmonary vein to the atrium. FIG. 1 shows the conductance profile 10 as the catheter was pulled back from a finger into the palm of the glove, then was pushed into a finger. As can be seen, the profile shows that the conductance of the palm was significantly larger than the conductance of the finger, and the transition or demarcation from the finger to the palm is apparent. Because conductance and cross-sectional area are proportional (as discussed below), conductance profile 10 is proportional to the CSA profile (not shown) and distinguishes between the smaller cross-sectional area of the fingers and the larger cross-sectional area of the palm.

Figure 2:
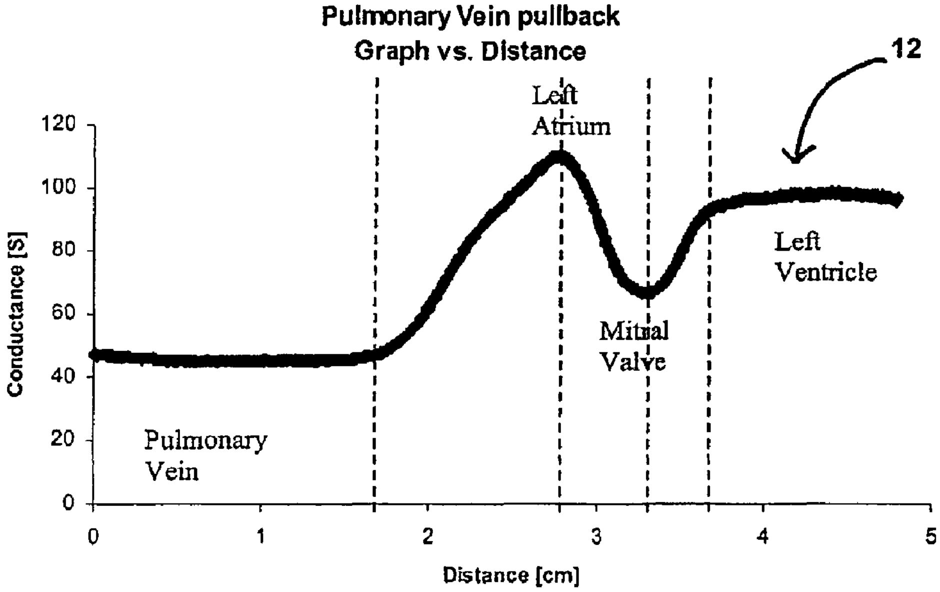
FIG. 2 shows the visual output of an embodiment of a catheter system for localization during an experiment of movement through an interior of a heart.

A similar pullback experiment was carried out in a heart. Starting from the pulmonary vein, a catheter configured for localization as described herein was pulled back from the pulmonary vein into the left atrium and ventricle. FIG. 2 shows a conductance tracing 12 that reflects the conductance for each region of the body lumen as the catheter is pulled back over a distance of about 5 cm from a starting point in the pulmonary vein. The pulmonary vein can be clearly identified by reference to its relative conductance compared to those of the left atrium, the mitral valve, and the left ventricle. Indeed, the atrial CSA is significantly larger than that of the pulmonary vein, and the atrial CSA increases with distance away from the pulmonary vein-atrial junction. A reduction in CSA is then observed as the catheter approaches and crosses the mitral valve. Once the catheter progresses through the mitral valve into the ventricle, the CSA increases gradually.

Using conductance data like that shown in FIG. 2, a clinician is able to locate the pulmonary vein-atrial junction, and then the tissue targeted for ablation, using a localization catheter as disclosed herein. For instance, once the end of the pulmonary vein is identified using the type of conductance data shown in FIG. 2 (i.e., where the conductance begins to increase), a 2 mm to 3 mm pullback will provide an appropriate region for ablation in most situations. The axial position of the catheter can be determined by the velocity of the pullback. The exact amount of necessary pullback should be determined by the clinician on a case by case basis based on the size of the patient and other relevant factors.

Figures 3A, 3B, 3C:
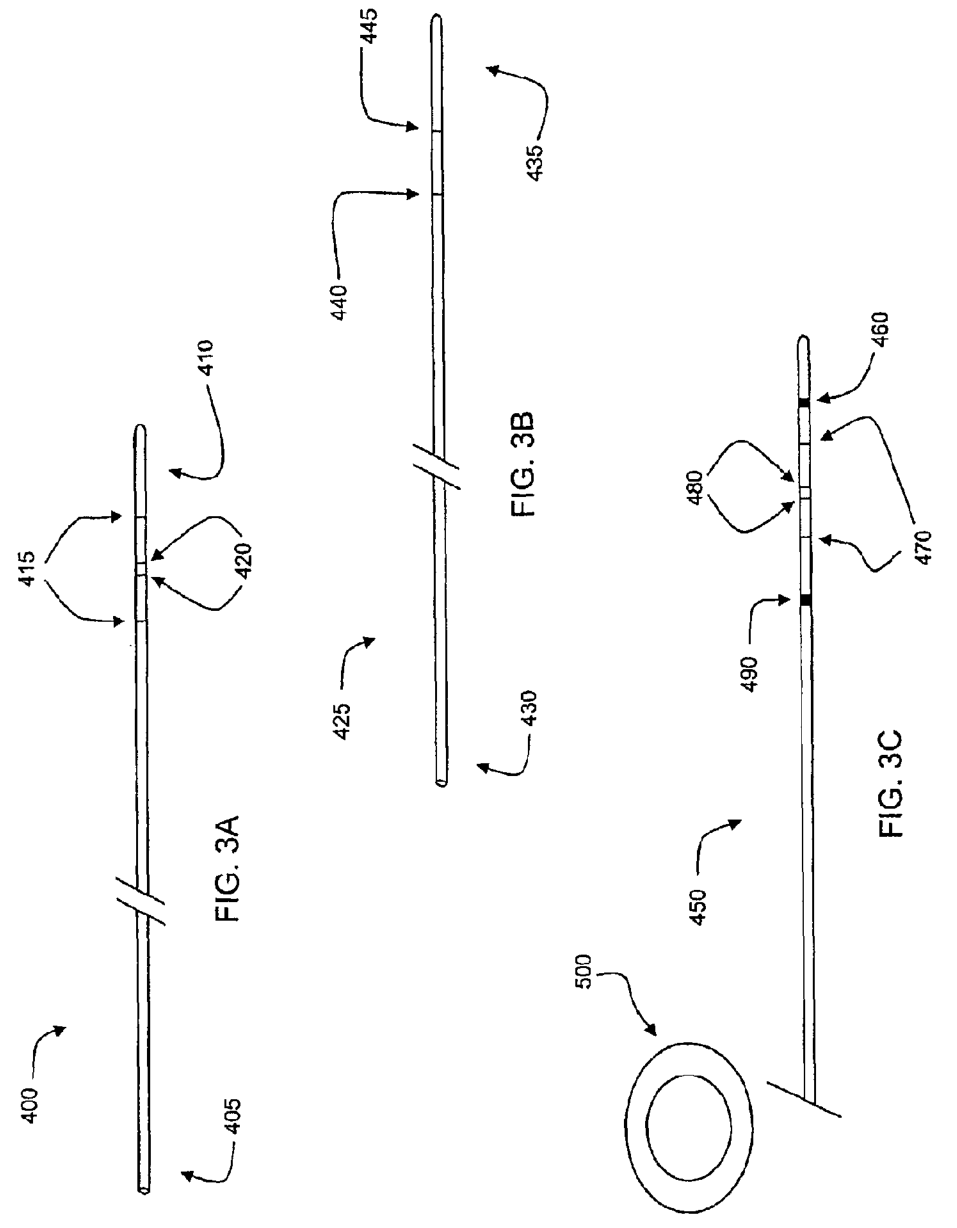
FIG. 3A shows an embodiment of a catheter for localization of a body lumen juncture.
FIG. 3B shows another embodiment of a catheter for localization of a body lumen juncture.
FIG. 3C shows an embodiment of a catheter for localization and ablation of a body lumen juncture.

A conductance or impedance catheter measures conductance within a body lumen using a number of electrodes. Referring now to FIG. 3A, there is shown a conductance catheter 400 configured to localize a body lumen junction using conductance measurements. Catheter 400 has a proximal end 405 and a distal end 410, which is suitable for introduction into a body lumen. In addition, catheter 400 includes a pair of excitation electrodes 415 and a pair of detection electrodes 420. Each of excitation electrodes 415 and detection electrodes 420 has a proximal end that is capable of attachment to a processing system (not shown) and a distal end that is located on catheter 400 between proximal end 405 and distal end 410. The distal ends of detection electrodes 420 are located on catheter 400 between the distal ends of excitation electrodes 415. Excitation electrodes 415 are configured to emit a measured electrical charge into the body lumen, while detection electrodes 420 detect the amount of the charge that travels through a fluid within the body lumen. As explained in more detail below, a processing system calculates the change in electrical charge to determine the conductance through the lumen at any given location in the lumen.

As shown in FIG. 3A, electrodes 415 and 420 are located at distal end 410 of catheter 400. However, the positioning of the electrodes is not limited to this distal end portion, but may be anywhere on the catheter that can assist in providing conductance information to the clinician. Furthermore, multiple sets of electrodes (see, e.g., FIG. 4F) may also be used to provide additional information used for mapping the interior anatomical structure of an internal organ, vessel, or other body lumen.

Many embodiments disclosed herein, such as the embodiment shown in FIG. 3A, have at least two detection electrodes and two excitation electrodes. However, in the embodiment shown in FIG. 3B, only two electrodes are used. Catheter 425 has a proximal end 430 and a distal end 435, as well as a first electrode 440 and a second electrode 445. Each of electrodes 440 and 445 has a proximal end (not shown) and a distal end located on catheter 425 between proximal end 430 and distal end 435. Because catheter 425 has only two electrodes, each electrode must serve both the excitation function and the detection function. To enable a single electrode to send and measure the electric charge, a delay must be added to the circuit. Additionally, a bipolar catheter must be stationary at the time of measurement, requiring the clinician to obtain a profile by moving the catheter to a desired location, stopping and taking a measurement, and then moving the catheter again. By contrast, tetrapolar catheters may take a continuous conductance measurement as the catheter is pulled or pushed through the body lumen, thereby giving a more detailed profile as compared to bipolar catheters.

Although the embodiments shown in FIG. 3A and FIG. 3B are used primarily for localization, certain of the disclosed embodiments combine the function of localization and ablation into one catheter and thereby improve the accuracy and safety of the ablation procedure by allowing the physician to properly identify the targeted tissue for ablation before the ablation begins. For example, catheter 450 shown in FIG. 3C is a conductance catheter that is configured to both localize a body lumen junction and ablate targeted tissue at or adjacent to the junction. Catheter 450 has an ablation contact 460 for removing or destroying a targeted tissue, two excitation electrodes 470, and two detection electrodes 480, as well as a passageway 490 for passing fluid through catheter 450 to the body lumen. Each of excitation electrodes 470 and detection electrodes 480 has a proximal end (not shown) for connection to a processor and a distal end positioned on catheter 450. The distal ends of detection electrodes 480 are positioned on catheter 450 between the distal ends of excitation electrodes 470.

Although at least some embodiments can properly measure lumen conductance in the presence of a bodily fluid (such as blood) within the lumen, certain other embodiments may use fluids injected into the body lumen to properly calculate lumen conductance and/or cross-sectional area, as explained herein. Therefore, some embodiments include a channel through which fluid is injected into the body lumen. In the embodiment shown in FIG. 3C, infusion passageway 490 is configured to permit such injection so that fluid flowing from passageway 490 will flow at least to the location of the distal ends of excitation electrodes 470 and detection electrodes 480. Thus, the fluid passing through passageway 490 into the lumen will come in contact with the distal ends of excitation electrodes 470 and detection electrodes 480.

Referring again to FIG. 3C, ablation contact 460 delivers an electric current to a tissue targeted for ablation. The current passes through ablation contact 460, which is in contact with the targeted tissue, entering the targeted tissue and returning to a grounding pad electrode 500 that is positioned on the outside of the body. Grounding pad electrode 500 may be held in place using any acceptable means, including an adhesive safe for contact with human skin. Although ablation contact 460 uses electrical current to destroy targeted tissue, other types of suitable ablation methods may be used. For instance, other embodiments disclosed herein could ablate tissue using very high heat, mechanical means, or cryoablation.

Referring now to FIGS. 4A to 4F, several embodiments of catheters are illustrated. With reference to the embodiment shown in FIG. 4A, there is shown an impedance catheter 22 with four electrodes 25, 26, 27, and 28 placed close to distal end 19 of the catheter. Electrodes 25 and 27 are excitation electrodes, while electrodes 26 and 28 are detection electrodes, thereby permitting measurement of conductance (and therefore calculation of cross-sectional area) during advancement of the catheter, as described in further detail below.

In addition, catheter 22 possesses an optional infusion passageway 35 located proximal to excitation electrode 25, as well as optional ports 36 for suction of contents of the body lumen or for infusion of fluid. The fluid to inject through passageway 35 or ports 36 can be any biologically compatible fluid, but, for some circumstances disclosed herein, the conductivity of the fluid is selected to be different from that of blood.

Figures 4A, 4B, 4C, 4D, 4E, 4F:
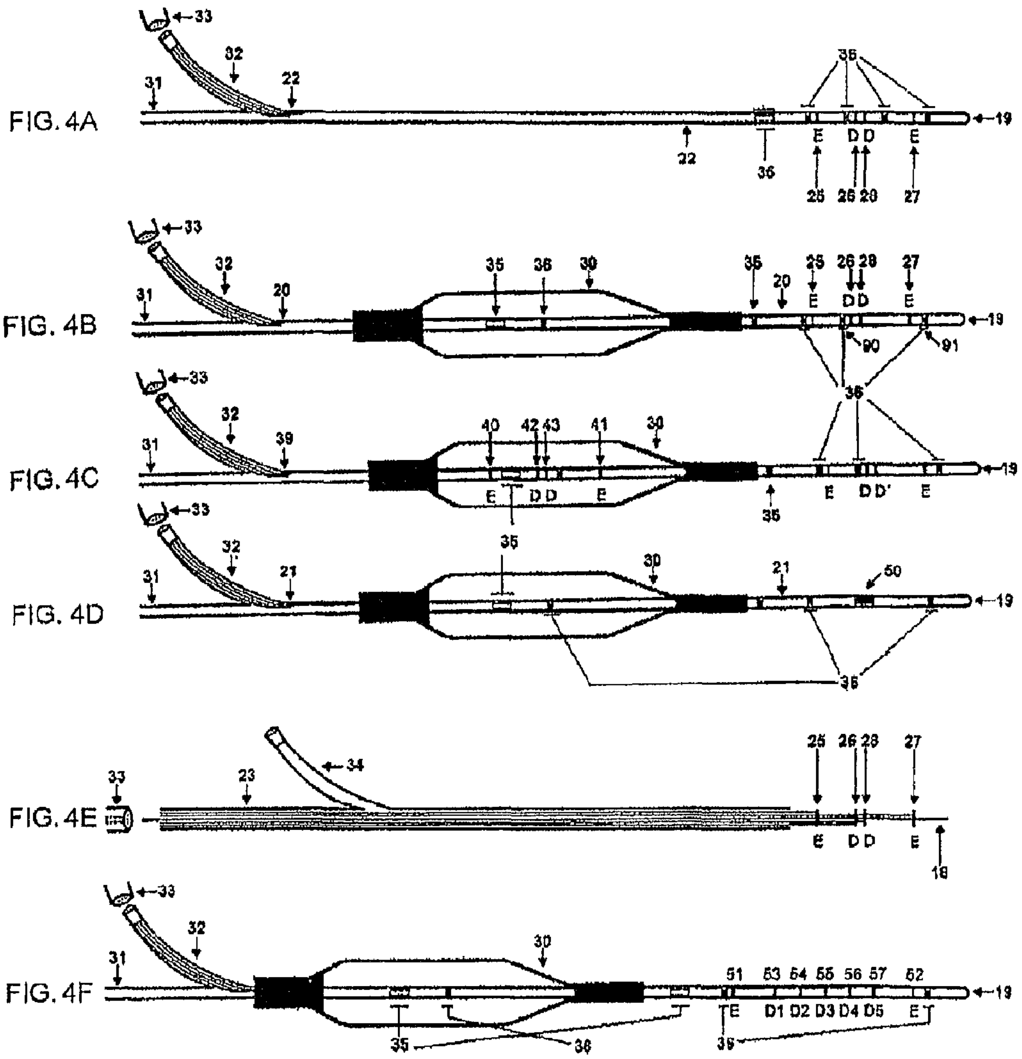
FIG. 4A shows another embodiment of a catheter for localization.
FIG. 4B shows an embodiment of a balloon catheter having impedance measuring electrodes supported in front of the stenting balloon.
FIG. 4C shows another embodiment of a balloon catheter having impedance measuring electrodes within and in front of the balloon.
FIG. 4D shows an embodiment of a catheter having an ultrasound transducer within and in front of the balloon.
FIG. 4E shows an embodiment of a guide catheter with wire and impedance electrodes.
FIG. 4F shows an embodiment of a catheter with multiple detection electrodes.

In various embodiments, including for example the embodiment shown in FIG. 4A, the catheter contains a channel 31 for insertion of a guide wire to stiffen the flexible catheter during insertion or data recording. Additionally, channel 31 may be used to inject fluid solutions of various concentrations (and various conductivities) into the body lumen of interest. An additional channel 32 may be connected to the catheter such that the electrical wires connected to the one or more electrodes on the catheter are directed through channel 32 and to a data processor, such as data processor system 100 (see FIG. 6), through an adaptor interface 33, such as an impedance module plug or the like, as described in more detail below.

In addition to localization and ablation, some embodiments disclosed herein provide other functionality. FIGS. 4B-4F show a number of embodiments of conductance catheters having various functions. For example, several such embodiments include an angioplasty balloon, in addition to impedance electrodes (see, e.g., FIG. 4B). Such catheters may include electrodes for accurate detection of organ luminal cross-sectional area and ports for pressure gradient measurements. Hence, when using such catheters, it is not necessary to change catheters during the procedure, as with the current use of intravascular ultrasound. In at least one embodiment, the catheter can provide direct measurement of the non-stenosed area of the lumen, thereby allowing the selection of an appropriately sized stent for implantation.

With reference to the embodiment shown in FIG. 4B, four wires were threaded through one of the two lumens of catheter 20 (a 4 Fr. catheter). Catheter 20 has a proximal end and a distal end 19, as well as excitation electrodes 25, 27 and detection electrodes 26, 28 placed at or near distal end 19. Proximal to these electrodes is an angioplasty or stenting balloon 30 capable of being used to treat stenosis. The distance between the balloon and the electrodes is usually small, in the 0.5 mm to 2 cm range, but can be closer or farther away, depending on the particular application or treatment involved. The portion of catheter 20 within balloon 30 includes an infusion passageway 35 and a pressure port 36.

Detection electrodes 26 and 28 are spaced 1 mm apart, while excitation electrodes 25 and 27 are spaced 4 mm to 5 mm from either side of the detection electrodes. The excitation and detection electrodes typically surround the catheter as ring electrodes, but they may also be point electrodes or have other suitable configurations. These electrodes may be made of any conductive material, such as platinum iridium or a material with a carbon-coated surface to avoid fibrin deposits. In at least one embodiment, the detection electrodes are spaced with 0.5 mm to 1 mm between them and with a distance of between 4 mm and 7 mm to the excitation electrodes on small catheters. On large catheters, for use in larger vessels and other larger body lumens, the electrode distances may be larger. The dimensions of the catheter selected for a treatment depend on the size of the vessel or other body lumen and are preferably determined in part on the results of finite element analysis.

In one approach, dimensions of a catheter to be used for any given application depend on the optimization of the potential field using finite element analysis described below. For small organs or in pediatric patients, the diameter of the catheter may be as small as 0.3 mm. In large organs, the diameter may be significantly larger depending on the results of the optimization based on finite element analysis. The balloon will typically be sized according to the preferred dimension of the organ after the distension. The balloon may be made of materials suitable for the function, such as, for example, polyethylene, latex, polyestherurethane, or combinations thereof. The thickness of the balloon will typically be on the order of a few microns. The catheter will typically be made of PVC or polyethylene, though other materials may be used equally well. The tip of the catheter can be straight, curved, or angled to facilitate insertion into the coronary arteries or other body lumens, such as, for example, the biliary tract.

Referring again to FIG. 4B, catheter 20 may also include several miniature pressure transducers (not shown) carried by the catheter or pressure ports for determining the pressure gradient proximal to the site where the conductance is measured. The pressure is preferably measured inside the balloon and proximal to, distal to, and at the location of the conductance measurement, and locations proximal and distal thereto, thereby enabling the measurement of pressure recordings at the site of stenosis and also the measurement of pressure-difference along or near the stenosis. In one embodiment, shown in FIG. 4B, catheter 20 includes pressure port 90 and pressure port 91 proximal to or at the site of the conductance measurement for evaluation of pressure gradients. As described below with reference to FIGS. 5A, 5B, and 6, in at least one embodiment, the pressure ports are connected by respective conduits in catheter 20 to pressure sensors in the data processor system 100 (see FIG. 6). Such pressure sensors are well known in the art and include, for example, fiber-optic systems, miniature strain gauges, and perfused low-compliance manometry.

In at least one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In another embodiment, shown in FIG. 4C, a catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27, and 28.

In various embodiments, the conductance may be measured using a two-electrode system (see FIG. 4D). In other embodiments, such as illustrated in FIG. 4F, the conductances at several locations can be measured at the same time using an array of five or more electrodes. Here, excitation electrodes 51, 52 are used to generate the current while detection electrodes 53, 54, 55, 56, and 57 are used to detect the current at their respective sites.

In another embodiment, shown in FIG. 4D, catheter 21 has one or more imaging or recording devices, such as, for example, ultrasound transducers 50 for cross-sectional area and wall thickness measurements. As shown, transducers 50 are located near distal end 19 of catheter 21.

With reference to the embodiment shown in FIG. 4E, electrodes 25, 26, 27, and 28 are built onto a wire 18, such as, for example, a pressure wire, and inserted through a guide catheter 23, where the infusion of a bolus can be made through the lumen of the guide catheter. Adaptor interface 33 may be used to house and guide the electrical wires (including proximal portions of the excitation and detection electrodes) to a data processor system 100, while a side channel 34 is used to inject various fluids into catheter 23. In yet another embodiment (not illustrated), the catheter includes a sensor for measurement of the flow of fluid in the body lumen.

Figure 9:
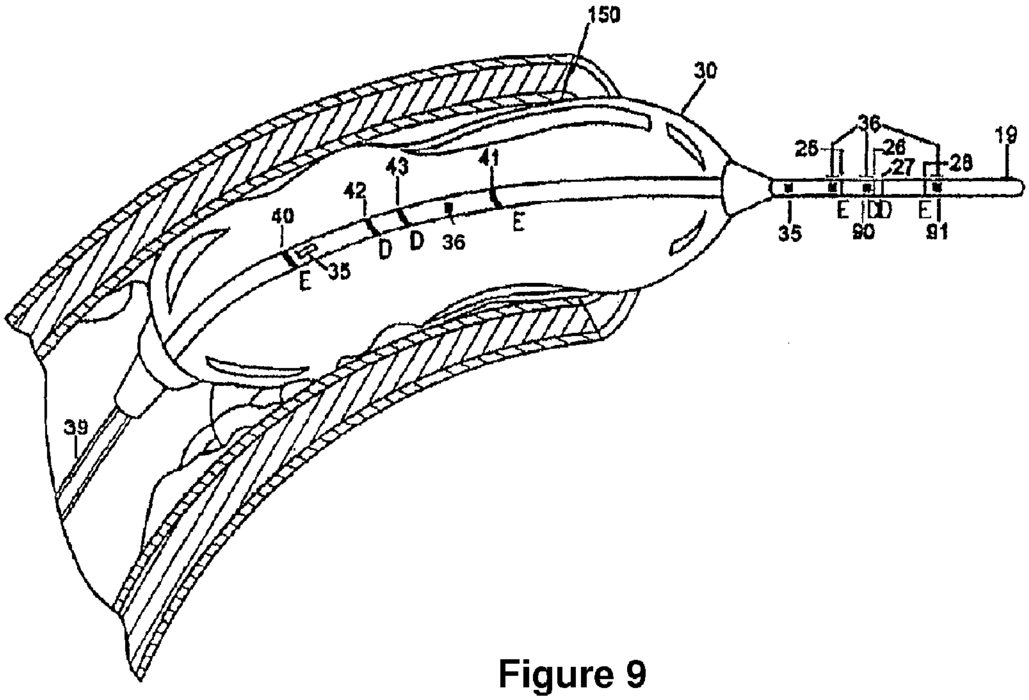
FIG. 9 shows balloon distension of the lumen of the coronary artery.
Figure 10:
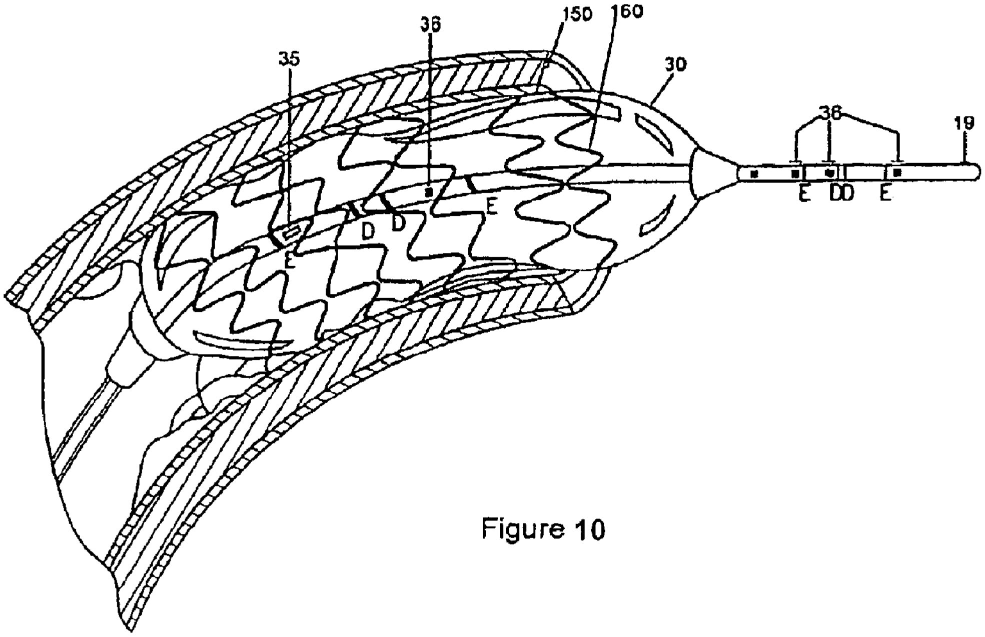
FIG. 10 shows balloon distension of a stent into the lumen of the coronary artery.

Referring now to the embodiment shown in FIG. 9, an angioplasty balloon 30 is shown distended within a coronary artery 150 for the treatment of stenosis. As described above with reference to FIG. 4C, a set of excitation electrodes 40, 41 and detection electrodes 42, 43 are located within angioplasty balloon 30. In another embodiment, shown in FIG. 10, angioplasty balloon 30 is used to distend a stent 160 within blood vessel 150.

Many of the embodiments described herein may be used as part of a system, which includes suitable connections between the system's various parts. As described below with reference to FIGS. 5A, 5B, and 6, the excitation and detection electrodes are electrically connected to electrically conductive leads in the catheter for connecting the electrodes to the data processor system 100.

Figure 5B:
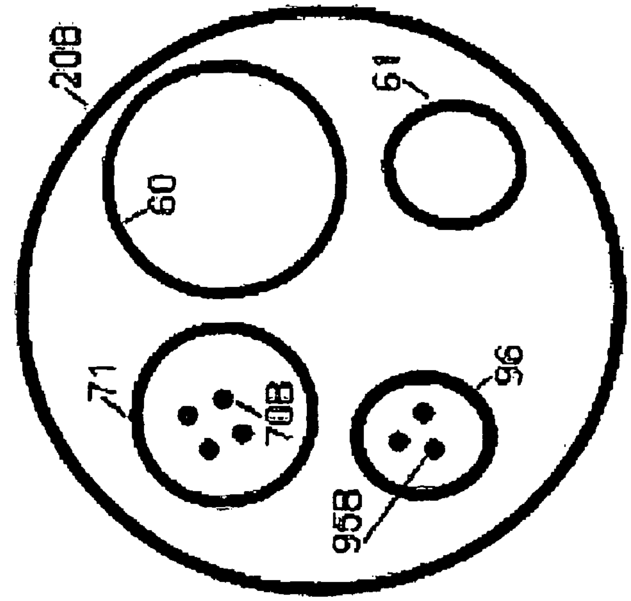
FIG. 5B shows another embodiment of a catheter in cross-section proximal to the location of the sensors showing the leads run in separate lumens.
Figure 5A:
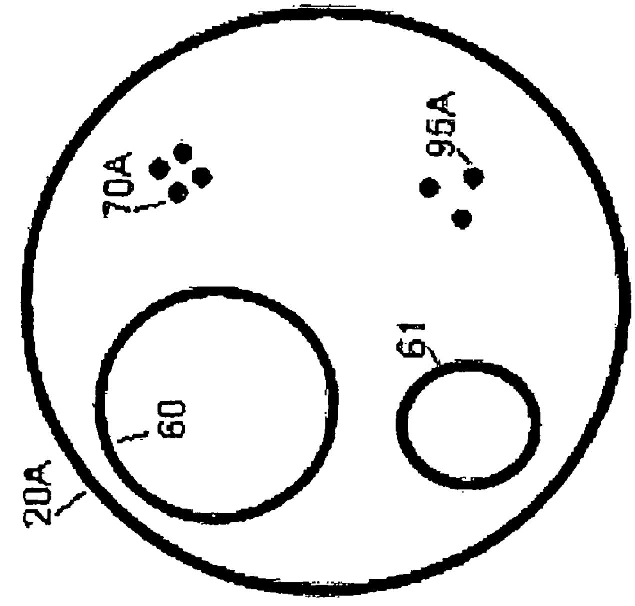
FIG. 5A shows an embodiment of a catheter in cross-section proximal to the location of the sensors showing the leads embedded in the material of the probe.

FIGS. 5A and 5B illustrate in cross-section two embodiments 20A and 20B of a catheter such as catheter 20 shown in FIG. 4B. Each embodiment has a lumen 60 for inflating and deflating the balloon and a lumen 61 for suction and infusion. The sizes of these lumens can vary. The electrode leads 70A are embedded in the material of the catheter in the embodiment shown in FIG. 5A, whereas the electrode leads 70B are tunneled through a lumen 71 formed within the body of catheter 20B shown in FIG. 5B.

Pressure conduits for perfusion manometry connect pressure ports 90, 91 to transducers included in the data processor system 100. As shown in FIG. 5A, pressure conduits 95A may be formed in catheter 20A. In another embodiment, shown in FIG. 5B, pressure conduits 95B constitute individual conduits within a tunnel 96 formed in catheter 20B. In the embodiments described above where miniature pressure transducers are carried by the catheter, electrical conductors may be substituted for these pressure conduits.

Figure 6:
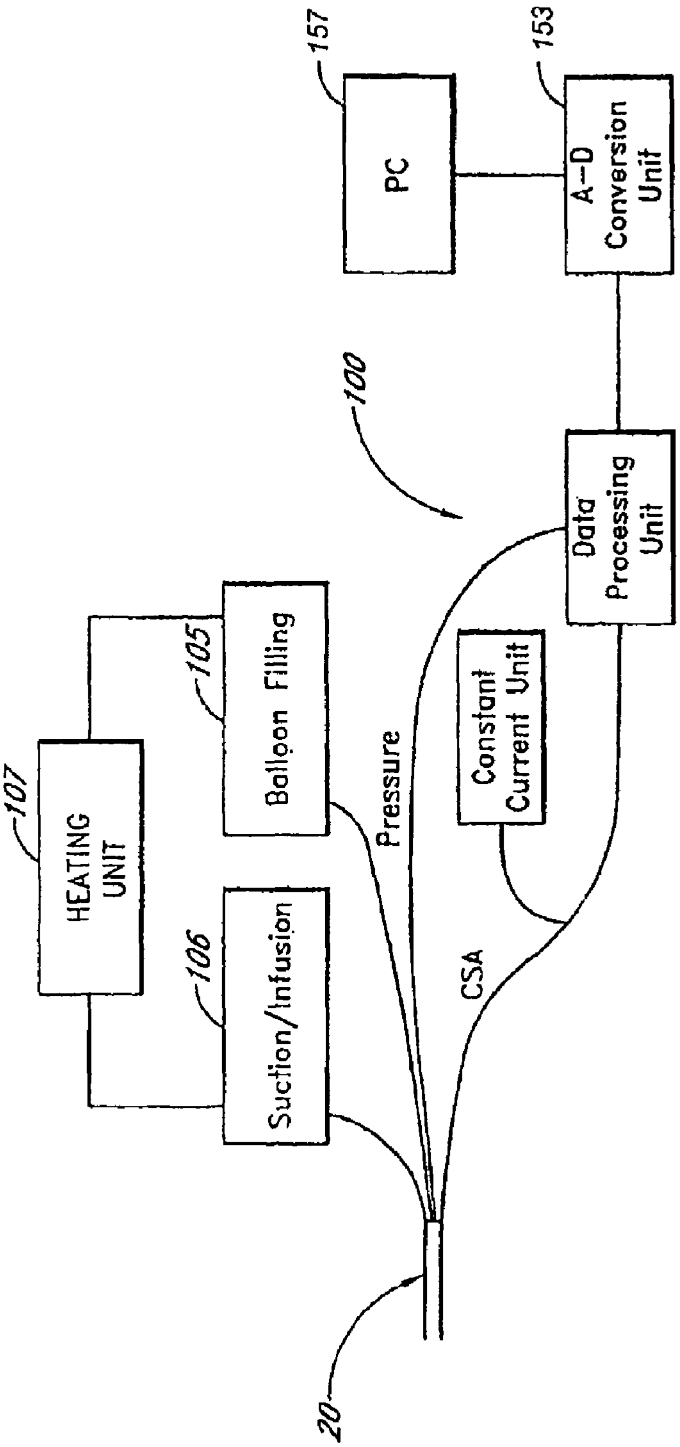
FIG. 6 is a schematic of an embodiment of a system showing a catheter carrying impedance measuring electrodes connected to a data processor equipment and excitation unit for the measurement of conductance and/or cross-sectional area.

With reference to FIG. 6, in at least some embodiments, catheter 20 connects to a data processor system 100, to a manual or automatic system 105 for distension of the balloon, and to a system 106 for infusion of fluid or suction of blood or other bodily fluid. The fluid for infusion may be heated with heating unit 107 to between 37° C. and 39° C. or to body temperature. The impedance planimetry system typically includes a constant current unit, amplifiers, and signal conditioners, but variations are possible. The pressure system typically includes amplifiers and signal conditioners. The system can optionally contain signal conditioning equipment for recording of fluid flow in the body lumen.

In at least one embodiment, the system is pre-calibrated and a catheter is available in a package. The package also may contain sterile syringes with fluids to be injected. The syringes are attached to the machine, and after heating of the fluid by the machine and placement of the catheter in the body lumen of interest, the user presses a button that initiates the injection with subsequent computation of the desired parameters. The CSA, parallel conductance, and/or other relevant measures, such as distensibility, tension, etc., will typically appear on the display panel in the PC module 157. The user can then remove the stenosis by distension or by placement of a stent.

If more than one CSA is measured at the same time, the system can contain a multiplexer unit or a switch between CSA channels. In at least one embodiment, each CSA measurement or pressure measurement will be through separate amplifier units.

In at least one embodiment, the impedance and pressure data are analog signals which are converted by analog-to-digital converters 153 and transmitted to a computer 157 for on-line display, on-line analysis, and storage. In other embodiments, all data handling is done on an entirely analog basis.

The processor system includes software programs for analyzing the conductance data. Additional software calculates cross-sectional areas based on a number of categories of data, as disclosed herein. However, as discussed in more detail below, to calculate for absolute cross-sectional values, certain errors must be reduced or eliminated. The software can be used to reduce the error in CSA values due to conductance of current in the lumen wall and surrounding tissue and to display the two-dimensional or three-dimensional geometry of the CSA distribution along the length of the vessel (and, optionally, along with the pressure gradient). In one embodiment of the software, a finite element approach or a finite difference approach is used to derive the CSA of organ stenosis, taking parameters such as conductivities of the fluid in the lumen and of the lumen wall and surrounding tissue into consideration.

In another embodiment, simpler circuits are used. As explained herein, absolute cross-sectional values may be calculated based on two or more injections of different NaCl solutions, which varies the conductivity of fluid in the lumen. In other embodiments, the software contains the code for reducing the error in luminal CSA measurement by analyzing signals during interventions, such as infusion of a fluid into the lumen or by changing the amplitude or frequency of the current from the current amplifier. The software chosen for a particular application may allow for computation of the CSA with only a small error instantly or within acceptable time during the medical procedure.

Referring now to FIG. 4A, catheter 22 measures conductance in the body lumen by detecting the change in voltage between detection electrodes 26, 28, as shown by the following equation:

$$\Delta V = \frac{I \cdot L}{C \cdot CSA} \quad [1a]$$

Thus, the change in voltage, ΔV, is equal to the magnitude of the current, I, multiplied by the distance between the detection electrodes, L, divided by the conductivity of the fluid in the lumen, C, and divided by the cross-sectional area, CSA. Because the current (I), the distance (L), and the conductivity (C) normally can be regarded as calibration constants during a localization procedure, an inversely proportional relationship exists between the voltage difference and the CSA, as shown by the following equation:

$$\Delta V = \frac{1}{CSA} \quad [1b]$$

In other words, as the cross-sectional area of the lumen decreases, the change in voltage measured by catheter 22 increases. As discussed earlier, conductance and cross-sectional area are proportional. Thus, this equation permits the relative conductances or cross-sectional areas of various intralumen anatomical structures to be determined from measurement of the change in voltage across the lumen using at least one excitation electrode and one detection electrode.

This measurement, however, does not produce accurate, or absolute, values of conductance or cross-sectional area because of the loss of current in the wall of the lumen and surrounding tissue. Although relying on the relative conductances or cross-sectional areas is sufficient for the localization of intraluminal structures, other embodiments for other purposes may require the accurate determination of absolute values for cross-sectional areas.

For example, accurate measures of the luminal cross-sectional area of organ stenosis within acceptable limits enables accurate and scientific stent sizing and placement. Proper stent implantation improves clinical outcomes by avoiding under or over deployment and under or over sizing of a stent, which can cause acute closure or in-stent re-stenosis. In at least one embodiment disclosed herein, an angioplasty or stent balloon includes impedance electrodes supported by the catheter in front of the balloon. These electrodes enable the immediate determination of the cross-sectional area of the vessel during the balloon advancement. This provides a direct measurement of non-stenosed area and allows the selection of the appropriate stent size. In one approach, error due to the loss of current in the wall of the organ and surrounding tissue is corrected by injection of two solutions of NaCl or other solutions with known conductivities. In another embodiment, impedance electrodes are located in the center of the balloon in order to deploy the stent to the desired cross-sectional area. These embodiments and procedures substantially improve the accuracy of stenting and the outcome of such stenting, as well as reduce overall costs.

Other embodiments make diagnosis of valve stenosis more accurate and more scientific by providing a direct, accurate measurement of cross-sectional area of the valve annulus, independent of the flow conditions through the valve. Thus, in such embodiments, the excitation and detection electrodes are embedded within a catheter to measure the valve area directly, independent of cardiac output or pressure drop, and therefore errors in the measurement of valve area are minimized. Further, pressure sensors may be mounted proximal and distal to the impedance electrodes to provide simultaneous pressure gradient recording.

Other embodiments improve evaluation of cross-sectional area and flow in organs like the gastrointestinal tract and the urinary tract At least some of the disclosed embodiments overcome the problems associated with determination of the size (cross-sectional area) of luminal organs, such as, for example, in the coronary arteries, carotid, femoral, renal and iliac arteries, aorta, gastrointestinal tract, urethra, and ureter. In addition, at least some embodiments also provide methods for registration of acute changes in wall conductance, such as, for example, due to edema or acute damage to the tissue, and for detection of muscle spasms/contractions.

The operation of catheter 20, shown in FIG. 4B, is as follows: for electrodes 25, 26, 27, 28, conductance of current flow through the organ lumen and organ wall and surrounding tissue is parallel; i.e., $$G(z, t) = \frac{CSA(z, t) \cdot C_b}{L} + G_p(z, t) \quad [2a]$$

where $G_p(z,t)$ is the effective conductance of the structure outside the bodily fluid (organ wall and surrounding tissue); $C_b$ is the specific electrical conductivity of the bodily fluid, which for blood generally depends on the temperature, hematocrit, and orientation and deformation of blood cells; and L is the distance between the detection electrodes. This equation shows that conductance, G(z,t), is proportional to the cross-sectional area, CSA (z,t). Thus, a larger conductance will reflect a larger cross-sectional area, and vice versa.

Equation [2a] can be rearranged to solve for cross-sectional area CSA(z,t), with a correction factor, α, if the electric field is non-homogeneous, as $$CSA(z,t) = \frac{L}{\alpha C_b}[G(z,t) - G_p(z,t)] \quad [2b]$$

where $\alpha$ would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [1a]. In one approach, finite element analysis is used to properly design the spacing between detection and excitation electrodes relative to the dimensions of the body lumen to provide a nearly homogenous field such that $\alpha$ can be considered equal to 1. Simulations show that a homogenous or substantially homogenous field is provided by (1) the placement of detection electrodes substantially equidistant from the excitation electrodes and (2) maintaining the distance between the detection and excitation electrodes substantially comparable to the body lumen diameter. In one approach, a homogeneous field is achieved by taking steps (1) and/or (2) described above so that $\alpha$ equals 1 in the foregoing analysis.

$G_p$ is a constant at any given position, z, along the long axis of a body lumen, and at any given time, t, in the cardiac cycle. Hence, two injections of different concentrations (and therefore conductivities) of NaCl solution give rise to two equations:

$$C_1 \cdot CSA(z,t) + L \cdot G_p(z,t) = L \cdot G_1(z,t) \quad [3]$$

$$C_2 \cdot CSA(z,t) + L \cdot G_p(z,t) = L \cdot G_2(z,t) \quad [4]$$

which can be solved simultaneously for CSA and $G_p$ as $$CSA(z,t) = L\frac{[G_2(z,t) - G_1(z,t)]}{[C_2 - C_1]} \quad [5]$$

$$G_p(z,t) = \frac{[C_2 \cdot G_1(z,t) - C_1 \cdot G_2(z,t)]}{[C_2 - C_1]} \quad [6]$$

where subscript "1" and subscript "2" designate any two injections of different NaCl concentrations (and conductivities). For each injection k, $C_k$ gives rise to $C_k$ which is measured as the ratio of the root mean square of the current divided by the root mean square of the voltage. The $C_k$ is typically determined through in vitro calibration for the various NaCl concentrations. The concentration of NaCl used is typically on the order of 0.45% to 1.8%. The volume of NaCl solution is typically about 5 ml, but the amount of solution should be sufficient to momentarily displace the entire local vascular blood volume or other body lumen fluid. The values of CSA(t) and $G_p(t)$ can be determined at end-diastole or end-systole (i.e., the minimum and maximum values) or the mean thereof. The value of CSA would vary through the cardiac cycle, but $G_p(t)$ does not vary significantly.

Once the CSA and $G_p$ of the body lumen are determined according to the above embodiment, rearrangement of Equation [2a] allows the calculation of the specific electrical conductivity of bodily fluid in the presence of fluid flow as $$C_b = \frac{L}{CSA(z,t)}[G(z,t) - G_p(z,t) \quad [7]$$

In this way, Equation [2b] can be used to calculate the CSA continuously (temporal variation, as for example through the cardiac cycle) in the presence of bodily fluid.

In one approach, a pull or push through is used to reconstruct the body lumen CSA along its length. During a long injection of solution (e.g., 10 s to 15 s), the catheter can be pulled back or pushed forward at constant velocity U. Equation [2a] can be expressed as $$CSA(U \cdot t, t) = \frac{L}{C_b}[G(U \cdot t, t) - G_p(U \cdot t, t)] \quad [8]$$

where the axial position, z, is the product of catheter velocity, U, and time, t; i.e., z=Ut.

For the two injections, denoted by subscript "1" and subscript "2", respectively, different time points $T_1$, $T_2$, etc. may be considered such that Equation [8] can be written as $$CSA_1(U \cdot T_1, t) = \frac{L}{C_1}[G_1(U \cdot T_1, t) - G_{p1}(U \cdot T_1, t)] \quad [9a]$$

$$CSA_1(U \cdot T_1, t) = \frac{L}{C_2}[G_2(U \cdot T_1, t) - G_{p1}(U \cdot T_1, t)] \quad [9b]$$

and $$CSA_2(U \cdot T_2, t) = \frac{L}{C_1}[G_1(U \cdot T_2, t) - G_{p2}(U \cdot T_2, t)] \quad [10a]$$

$$CSA_2(U \cdot T_2, t) = \frac{L}{C_2}[G_2(U \cdot T_2, t) - G_{p2}(U \cdot T_2, t)] \quad [10b]$$

and so on. Each set of Equations [9a], [9b] and [10a], [10b], etc., can be solved for $CSA_1$, $G_p1$ and $CSA_2$, $G_p2$, respectively. Hence, one can measure the CSA at various time intervals and therefore at different positions along the body lumen to reconstruct the length of the lumen. In at least one embodiment, the data on the CSA and parallel conductance as a function of longitudinal position along the body lumen can be exported from an electronic spreadsheet, such as, for example, a Microsoft Excel file, to diagramming software, such as AutoCAD®, where the software uses the coordinates to render a three-dimensional depiction of the lumen on the monitor.

For example, in one approach, the pull back reconstruction was made during a long injection where the catheter was pulled back at constant rate by hand. The catheter was marked along its length such that the pull back was made at 2 mm/sec. Hence, during a 10-second injection, the catheter was pulled back about 2 cm. The data was continuously measured and analyzed at every two second interval; i.e., at every 4 mm. Thus, six different measurements of CSA and $G_p$ were taken which were used to reconstruct the CSA and $G_p$ along the length of the 2 cm segment.

In one approach, the wall thickness is determined from the parallel conductance for those body lumens that are surrounded by air or non-conducting tissue. In such cases, the parallel conductance is equal to $$G_p = \frac{CSA_w \cdot C_w}{L} \quad [11a]$$

where $CSA_w$ is the CSA of the lumen wall and $CSA_w$ is the electrical conductivity of the wall. This equation can be solved for $CSA_w$ as $$CSA_w = \frac{G_p \cdot L}{C_w} \quad [11b]$$

For a cylindrical body lumen, the wall thickness, h, can be expressed as $$h = \frac{CSA_w}{\pi D} \quad [12]$$

where D is the diameter of the lumen, which can be determined from the circular CSA($D=[4CSA/\pi]^{1/2}$).

When the CSA, pressure, wall thickness, and flow data are determined according to the embodiments outlined above, it is possible to compute the compliance (e.g., $\Delta CSA/\Delta AP$), tension (e.g., P*r, where P and r are the intraluminal pressure and radius of a cylindrical lumen), stress (e.g., P*r/h, where h is the wall thickness of the cylindrical organ), strain (e.g., $(C-C_d)/C_d$ where C is the inner circumference and $C_d$ is the circumference in diastole), and wall shear stress (e.g., $4\ \mu Q/r^3$ where μ, Q, and r are the fluid viscosity, flow rate, and radius of the cylindrical lumen for a fully developed flow). These quantities can be used in assessing the mechanical characteristics of the system in health and disease.

In at least one approach for localization or measuring the conductance (and determining the cross-sectional area) of a body lumen, a catheter is introduced from an exteriorly accessible opening (for example, the mouth, nose, or anus for GI applications, or the mouth or nose for airway applications) into the targeted body lumen. For cardiovascular applications, the catheter can be inserted into the lumens in various ways, such as, for example, those used in conventional angioplasty. In at least one embodiment, an 18 gauge needle is inserted into the femoral artery followed by an introducer. A guide wire is then inserted into the introducer and advanced into the lumen of the femoral artery. A 4 or 5 Fr. conductance catheter is then inserted into the femoral artery via wire, and the wire is subsequently retracted. The catheter tip containing the conductance electrodes can then be advanced to the region of interest by use of x-ray (e.g., fluoroscopy). In another approach, this methodology is used on small to medium size vessels (e.g., femoral, coronary, carotid, iliac arteries).

In one approach, a minimum of two injections with different concentrations of NaCl (and, therefore, different conductivities) are required to solve for the two unknowns, CSA and $G_p$. However, in other embodiments disclosed herein, only relative values for conductance or cross-sectional area are necessary, so the injection of two solutions is not necessary. In another approach, three injections will yield three sets of values for CSA and $G_p$ (although not necessarily linearly independent), while four injections would yield six sets of values. In one approach, at least two solutions (e.g., 0.5% and 1.5% NaCl solutions) are injected in the targeted vessel or other lumen. Studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the lumen flow rate.

In at least one approach, involving the application of Equations [5] and [6], the vessel is under identical or very similar conditions during the two injections. Hence, some variables, such as the infusion rate, bolus temperature, etc., are similar for the two injections. Typically, a short time interval is to be allowed (1 to 2 minute period) between the two injections to permit the vessel to return to homeostatic state. This can be determined from the baseline conductance as shown in FIG. 7A, 7B, 8A, or 8B. The parallel conductance is preferably the same or very similar during the two injections. Dextran, albumin, or another large molecular weight molecule may be added to the NaCl solutions to maintain the colloid osmotic pressure of the solution to reduce or prevent fluid or ion exchange through the vessel wall.

In one approach, the NaCl solution is heated to body temperature prior to injection since the conductivity of current is temperature dependent. In another approach, the injected bolus is at room temperature, but a temperature correction is made since the conductivity is related to temperature in a linear fashion.

In one approach, a sheath is inserted through either the femoral artery or the carotid artery in the direction of flow. To access the lower anterior descending ("LAD") artery, the sheath is inserted through the ascending aorta. For the carotid artery, where the diameter is typically on the order of 5 mm to 5.5 mm, a catheter having a diameter of 1.9 mm can be used, as determined from finite element analysis, discussed further below. For the femoral and coronary arteries, where the diameter is typically in the range from 3.5 mm to 4 mm, so a catheter of about 0.8 mm diameter would be appropriate. The catheter can be inserted into the femoral, carotid, or LAD artery through a sheath appropriate for the particular treatment. Measurements for all three vessels can be made similarly.

Described here are the protocol and results for one approach that is generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37° C. A 5 ml to 10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab® was used to analyze the data including filtering with high pass and with low cut off frequency (1200 Hz). The data was displayed using Matlab®, and the mean of the voltage signal during the passage of each respective solution was recorded. The corresponding currents were also measured to yield the conductance (G=I/V). The conductivity of each solution was calibrated with six different tubes of known CSA at body temperature. A model using Equation [1a] was fitted to the data to calculate conductivity C. The analysis was carried out with SPSS statistical software using the non-linear regression fit. Given C and G for each of the two injections, an Excel spreadsheet file was formatted to calculate the CSA and $G_p$ as per equations [5] and [6], respectively. These measurements were repeated several times to determine the reproducibility of the technique. The reproducibility of the data was within 5%. Ultrasound was used to measure the diameter of the vessel simultaneous with our conductance measurements. The detection electrodes were visualized with ultrasound, and the diameter measurements was made at the center of the detection electrodes. The maximum differences between the conductance and ultrasound measurements were within 10%.

FIGS. 7A, 7B, 8A, and 8B illustrate voltage measurements in the blood stream in the left carotid artery. Here, the data acquisition had a sampling frequency of 75 KHz, with two channels—the current injected and the detected voltage, respectively. The current injected has a frequency of 5 KHz, so the voltage detected, modulated in amplitude by the impedance changing through the bolus injection, will have a spectrum in the vicinity of 5 KHz.

Figure 7A:
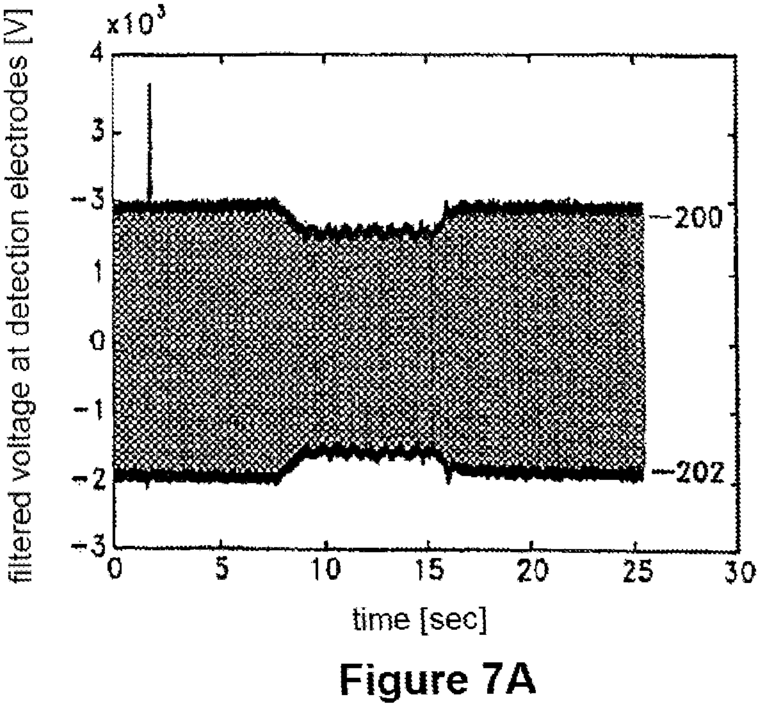
FIG. 7A shows the detected filtered voltage drop as measured in the blood stream before and after injection of 1.5% NaCl solution.
Figure 7B:
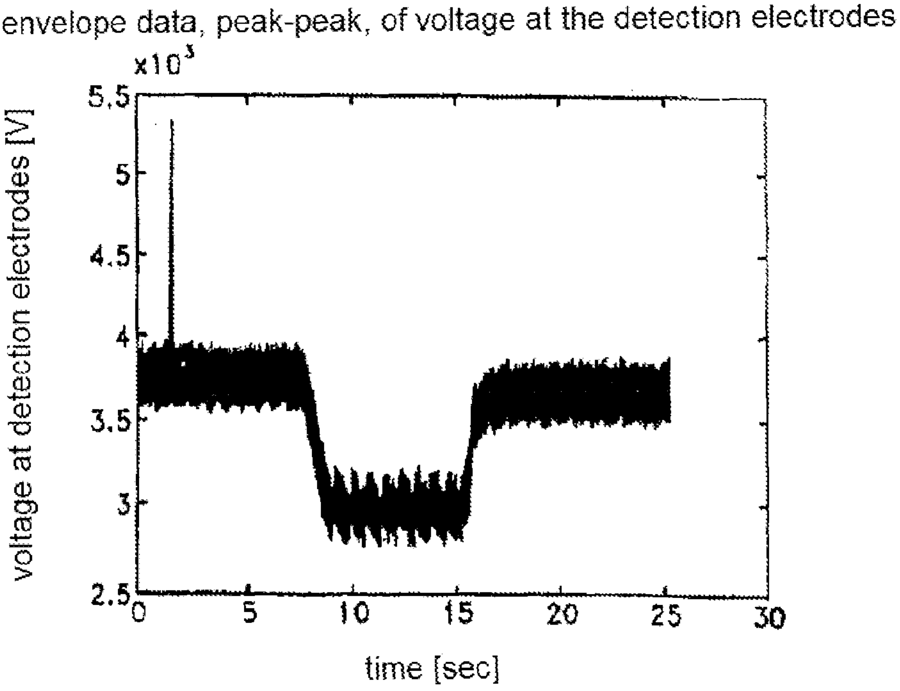
FIG. 7B shows the peak-to-peak envelope of the detected voltage shown in FIG. 7A.
Figure 8A:
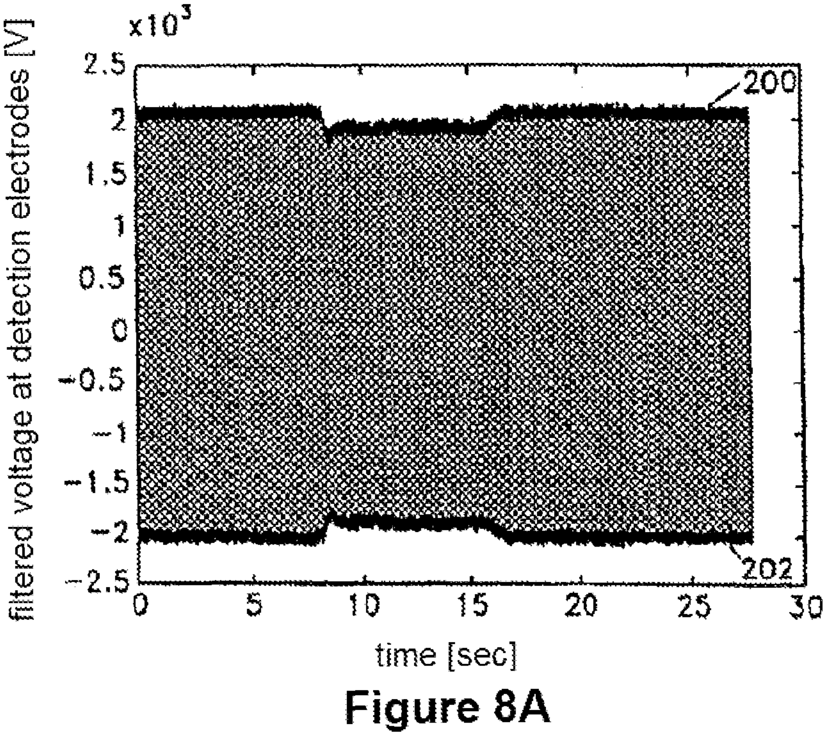
FIG. 8A shows the detected filtered voltage drop as measured in the blood stream before and after injection of 0.5% NaCl solution.
Figure 8B:
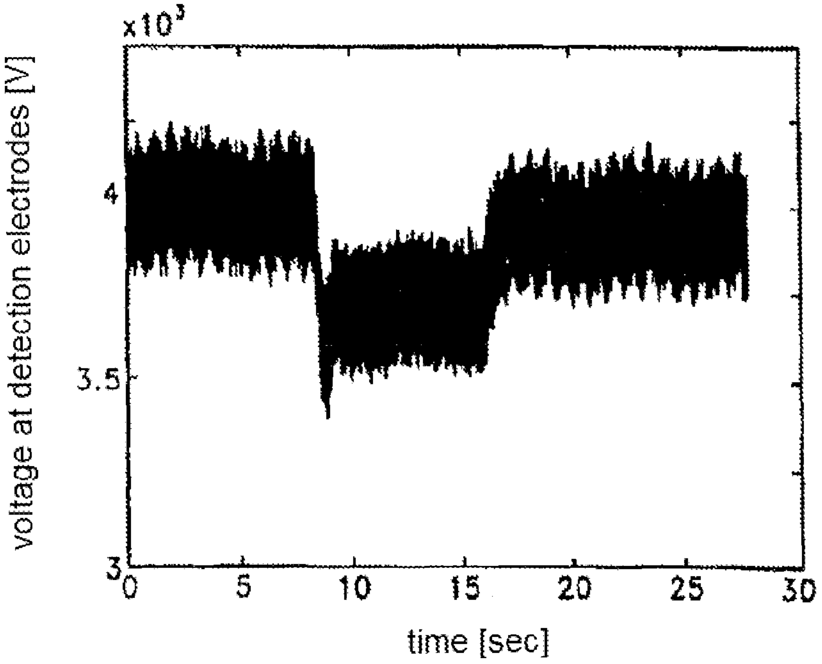
FIG. 8B shows the peak-to-peak envelope of the detected voltage shown in FIG. 8A.

With reference to FIG. 7A there is shown a signal processed with a high pass filter with low cut off frequency (1200 Hz). The top and bottom portions 200, 202 show the peak-to-peak envelope detected voltage which is displayed in FIG. 7B. The initial 7 seconds correspond to the baseline; i.e., electrodes in the blood stream. The next 7 seconds correspond to an injection of hyper-osmotic NaCl solution (1.5% NaCl). It can be seen that the voltage is decreased, implying increased conductance (since the injected current is constant). Once the NaCl solution is washed out, the baseline is recovered as shown in FIGS. 7A and 7B. FIGS. 8A and 8B show similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 7A, 7B and 8A, 8B, respectively). This allows determination of the variation of CSA throughout the cardiac cycle as outline above.

The NaCl solution can be injected by hand or by using a mechanical injector to momentarily displace the entire volume of blood or bodily fluid in the lumen segment of interest. For example, in a blood vessel, the pressure generated by the injection will not only displace the blood in the antegrade direction (in the direction of blood flow) but also in the retrograde direction (by momentarily pushing the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. It will be understood that any bifurcation(s) (with branching angle near 90 degrees) near the targeted lumen can cause an overestimation of the calculated CSA. Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In one approach, error due to the eccentric position of the electrode or other imaging device can be reduced by inflation of a balloon on the catheter. The inflation of the balloon during measurement will place the electrodes or other imaging device in the center of the vessel away from the wall. In the case of impedance electrodes, the inflation of the balloon can be synchronized with the injection of a bolus such that the balloon inflation would immediately precede the bolus injection. Our results, however, show that the error due to catheter eccentricity is small.

The CSA predicted by Equation [5] corresponds to the area of the vessel or other lumen external to the catheter (i.e., CSA of vessel minus CSA of catheter). If the conductivity of the NaCl solutions is determined by calibration from Equation [1a] with various tubes of known CSA, then the calibration accounts for the dimension of the catheter and the calculated CSA corresponds to that of the total vessel lumen. In at least one embodiment, the calibration of the CSA measurement system will be performed at 37° C. by applying 100 mmHg in a solid polyphenolenoxide block with holes of known CSA ranging from 7.065 $mm^2$ (3 mm in diameter) to 1017 $mm^2$ (36 mm in diameter). If the conductivity of the solutions is obtained from a conductivity meter independent of the catheter, however, then the CSA of the catheter is generally added to the CSA computed from Equation [5] to give the total CSA of the vessel.

The signals are generally non-stationary, nonlinear, and stochastic. To deal with non-stationary stochastic functions, one can use a number of methods, such as the Spectrogram, the Wavelet's analysis, the Wigner-Ville distribution, the Evolutionary Spectrum, Modal analysis, or the intrinsic model function ("IMF") method. The mean or peak-to-peak values can be systematically determined by the aforementioned signal analysis and used in Equation [5] to compute the CSA.

For the determination of conductance or cross-sectional area of a heart valve, it is generally not feasible to displace the entire volume of the heart. Hence, the conductivity of the blood is transiently changed by injection of a hypertonic NaCl solution into the pulmonary artery. If the measured total conductance is plotted versus blood conductivity on a graph, the extrapolated conductance at zero conductivity corresponds to the parallel conductance. In order to ensure that the two inner electrodes are positioned in the plane of the valve annulus (2 mm to 3 mm), in one embodiment, two pressure sensors 36 are placed immediately proximal and distal to (1 mm to 2 mm above and below, respectively) the detection electrodes or sets of detection electrodes (see, e.g., FIGS. 4A and 4F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen, which has low electrical conductivity. In another application, a pull back or push forward through the heart chamber will show different conductance due to the change in geometry and parallel conductance. This can be established for normal patients, which can then be used to diagnose valvular stenosis.

In one approach, for the esophagus or the urethra, the procedures can conveniently be done by swallowing fluids of known conductivities into the esophagus and infusion of fluids of known conductances into the urinary bladder followed by voiding the volume. In another approach, fluids can be swallowed or urine voided followed by measurement of the fluid conductivities from samples of the fluid. The latter method can be applied to the ureter where a catheter can be advanced up into the ureter and fluids can be injected from a proximal port on the probe (will also be applicable in the intestines) or urine production can be increased and samples taken distal in the ureter during passage of the bolus or from the urinary bladder.

In one approach, concomitant with measuring the conductance, cross-sectional area, and/or pressure gradient at the treatment or measurement site, a mechanical stimulus is introduced by way of inflating the balloon or by releasing a stent from the catheter, thereby facilitating flow through the stenosed part of the lumen. In another approach, concomitant with measuring the conductance, cross-sectional area, and/or pressure gradient at the treatment site, one or more pharmaceutical substances for diagnosis or treatment of stenosis is injected into the treatment site. For example, in one approach, the injected substance can be a smooth muscle agonist or antagonist. In yet another approach, concomitant with measuring the conductance, cross-sectional area, and/or pressure gradient at the treatment site, an inflating fluid is released into the treatment site for release of any stenosis or materials causing stenosis in the lumen or treatment site.

Again, it will be noted that the methods, systems, and catheters described herein can be applied to any body lumen or treatment site. For example, the methods, systems, and catheters described herein can be applied to any one of the following hollow bodily systems: the cardiovascular system including the heart; the digestive system; the respiratory system; the reproductive system; and the urogenital tract.

Finite Element Analysis: In one preferred approach, finite element analysis (FEA) is used to verify the validity of Equations [5] and [6]. There are two major considerations for the model definition: geometry and electrical properties. The general equation governing the electric scalar potential distribution, V, is given by Poisson's equation as:

$$\nabla\cdot(C\nabla V)=-1 \qquad [13]$$

where C, I and ∇ are the conductivity, the driving current density, and the del operator, respectively. Femlab or any standard finite element package can be used to compute the nodal voltages using Equation [13]. Once V has been determined, the electric field can be obtained from $E=-\nabla V$.

The FEA allows the determination of the nature of the field and its alteration in response to different electrode distances, distances between driving electrodes, wall thicknesses, and wall conductivities. The percentage of total current in the lumen of the vessel (% I) can be used as an index of both leakage and field homogeneity. Hence, the various geometric and electrical material properties can be varied to obtain the optimum design, i.e., minimizing the non-homogeneity of the field. Furthermore, the experimental procedure was simulated by injection of the two solutions of NaCl to verify the accuracy of Equation [5]. Finally, the effect of the presence of electrodes and the catheter in the lumen of vessel was assessed. The error terms representing the changes in measured conductance due to the attraction of the field to the electrodes and the repulsion of the field from the resistive catheter body were quantified.

Poisson's equation was solved for the potential field, which takes into account the magnitude of the applied current, the location of the current driving and detection electrodes, and the conductivities and geometrical shapes in the model including the vessel wall and surrounding tissue. This analysis suggests that the following conditions are optimal for the cylindrical model: (1) the placement of detection (voltage sensing) electrodes equidistant from the excitation (current driving) electrodes; (2) the distance between the excitation electrodes should be much greater than the distance between the detection electrodes; and (3) the distance between the detection and excitation electrodes is comparable to the vessel diameter, or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one approach, one or more of conditions (1)-(3) described above are met to increase the accuracy of the cylindrical model.

Figure 11A:
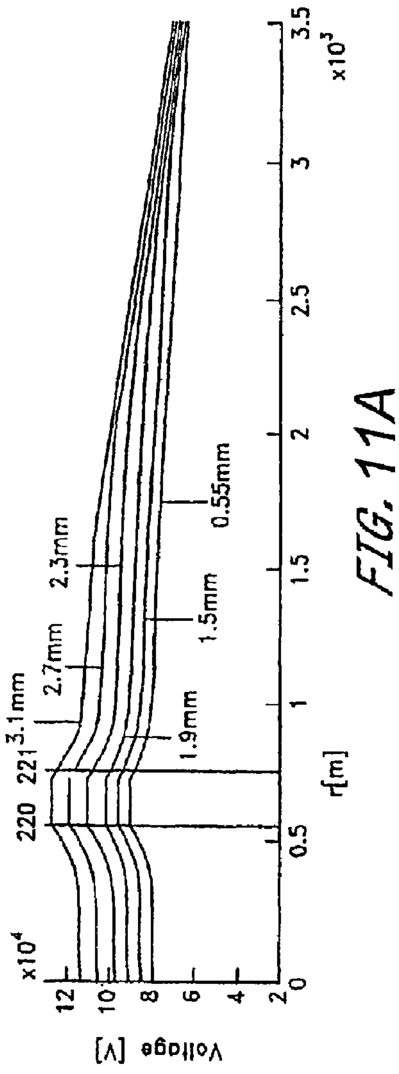
FIG. 11A shows the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site.
Figure 11B:
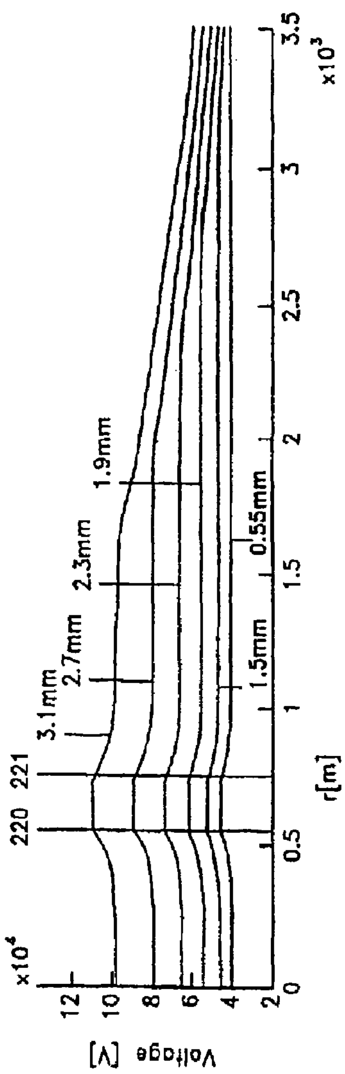
FIG. 11B shows the voltage recorded by a conductance catheter with a radius of 0.55 mm for various size vessels (vessel radii of 3.1, 2.7, 2.3, 1.9, 1.5 and 0.55 mm for the six curves, respectively) when a 1.5% NaCl bolus is injected into the treatment site.

Theoretically, it is impossible to ensure a completely homogeneous field given the current leakage through the lumen wall into the surrounding tissue. It was found that the iso-potential line is not constant as one moves out radially along the vessel as stipulated by the cylindrical model. FIGS. 11A and 11B show the detected voltage for a catheter with a radius of 0.55 mm for two different NaCl solutions (0.5% and 1.5%, respectively). The origin corresponds to the center of the catheter. The first vertical line 220 represents the inner part of the electrode which is wrapped around the catheter, and the second vertical line 221 is the outer part of the electrode in contact with the solution (diameter of electrode is approximately 0.25 mm). The six different curves, top to bottom, correspond to six different vessels with radii of 3.1 mm, 2.7 mm, 2.3 mm, 1.9 mm, 1.5 mm, and 0.55 mm, respectively. It can be seen that a "hill" 220, 221 occurs at the detection electrodes, followed by a fairly uniform plateau in the vessel lumen, followed by an exponential decay into the surrounding tissue. Since the potential difference is measured at the detection electrode 220, 221, the simulation generates the "hill" whose value corresponds to the equivalent potential in the vessel as used in Equation [5]. Thus, for each catheter size, the dimension of the vessel was varied such that Equation [5] was exactly satisfied. Consequently, the optimum catheter size for a given vessel diameter was obtained such that the distributive model satisfies the lumped equations (Equations [5] and [6]). In this way, a relationship between vessel diameter and catheter diameter can be generated such that the error in the CSA determination is less than 5%. In one embodiment, different diameter catheters are prepackaged and labeled for optimal use in certain size vessel. For example, for vessel dimensions in the range of 4 mm to 5 mm, 5 mm to 7 mm, or 7 mm to 10 mm, analysis shows that optimum diameter catheters will be in the range of 0.9 mm to 1.4 mm, 1.4 mm to 2 mm, or 2 mm to 4.6 mm, respectively. The clinician can select the appropriate diameter catheter based on the estimated vessel diameter of interest. This decision will be made prior to the procedure and will serve to minimize the error in the determination of lumen CSA.

Thus, a number of the embodiments disclosed herein accurately calculate lumen cross-sectional area by measuring conductance and correcting for various errors inherent in such measurements. However, at least some of the disclosed embodiments provide for the localization of body lumen junctions and other intraluminal anatomical structures using relative conductances and/or cross-sectional areas. Because only relative differences in conductance or cross-sectional area are necessary for accurate localization, the calculation of absolute values for various locations within the body lumen may be skipped in most instances.

Percutaneous access to the pericardial space may be obtained using devices and methods disclosed in International Patent Application No. PCT/US2007/015207, filed Jun. 29, 2007, the contents of which are incorporated herein by reference. Although navigation to the pericardial space from the intravascular region (inside of the heart) provides more certainty of position of vital cardiac structures than does intrathoracic access (from outside of the heart), access to the pericardial space may be obtained by any suitable method.

Figure 12B:
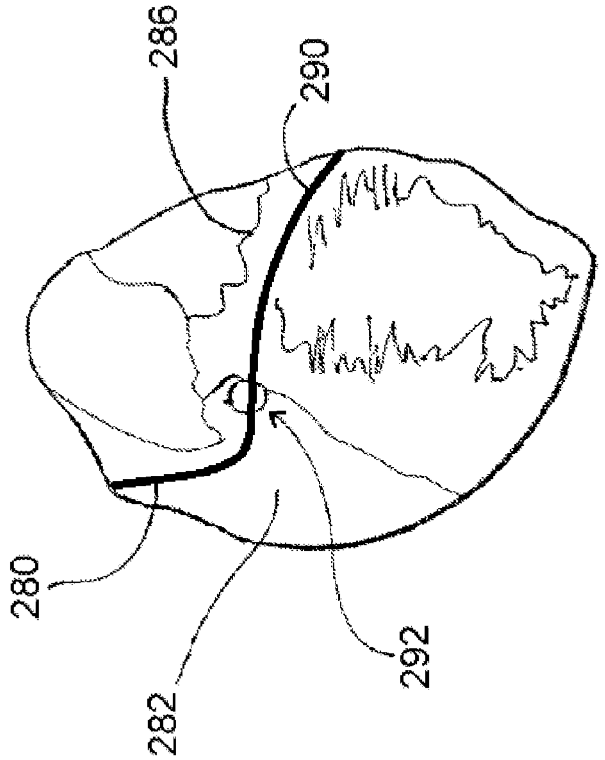
FIG. 12B shows a percutaneous intravascular pericardial delivery using another embodiment of an engagement catheter and another embodiment of a delivery catheter as disclosed herein.
Figure 12A:
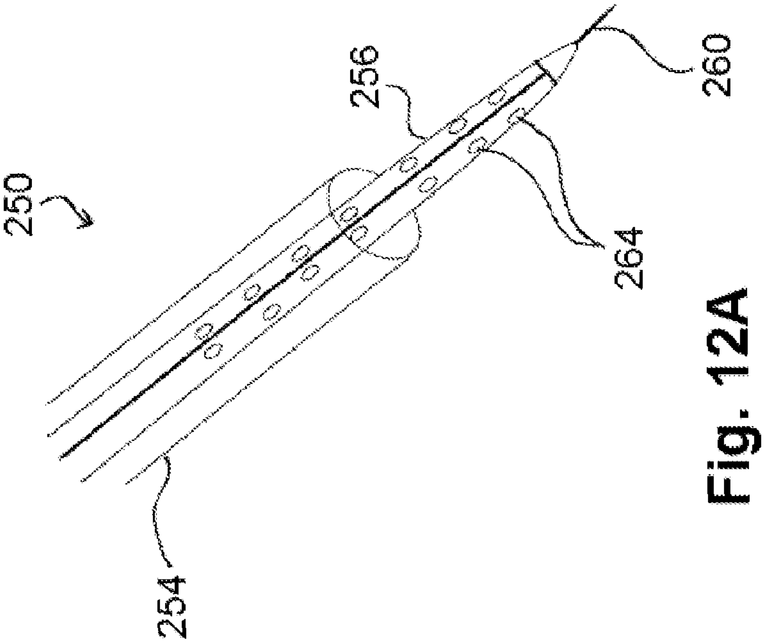
FIG. 12A shows an embodiment of an engagement catheter and an embodiment of a delivery catheter as disclosed herein.

In the embodiment of the catheter system shown in FIG. 12A, catheter system 250 includes an engagement catheter 254, a delivery catheter 256, and a needle 260. Although each of engagement catheter 254, delivery catheter 256, and needle 260 has a proximal end and a distal end, FIG. 12A shows only the distal end. Engagement catheter 254 has a lumen through which delivery catheter 256 has been inserted, and delivery catheter 256 has a lumen through which needle 260 has been inserted. Delivery catheter 256 also has a number of openings 264 that can be used to transmit fluid from the lumen of the catheter to the heart tissue in close proximity to the distal end of the catheter.

Figures 13A, 13B, 13C:
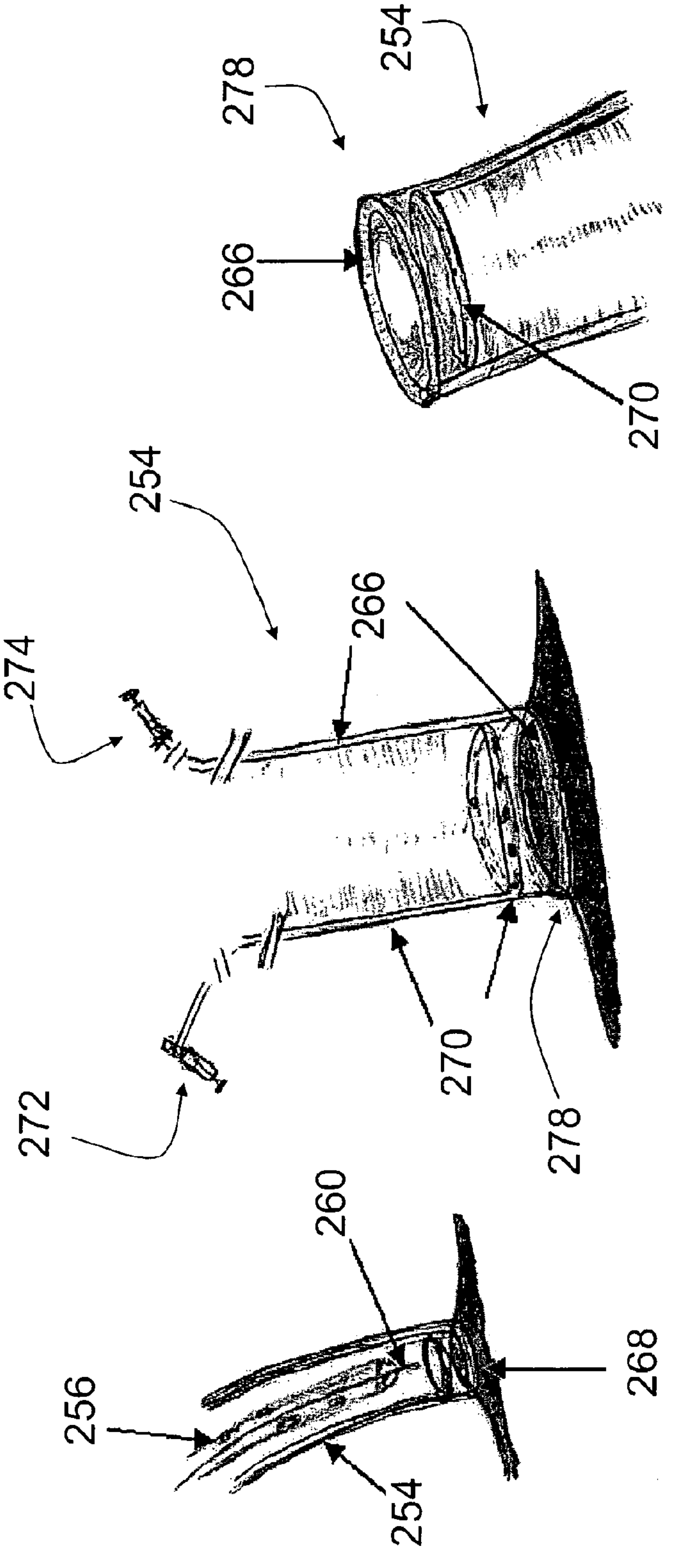
FIG. 13A shows a percutaneous intravascular technique for accessing the pericardial space through a right atrial wall or atrial appendage using the engagement and delivery catheters shown in FIG. 12A.
FIG. 13B shows the embodiment of an engagement catheter shown in FIG. 2A.
FIG. 13C shows another view of the distal end of the engagement catheter embodiment shown in FIGS. 13A and 13B.

As shown in more detail in FIGS. 13A, 13B, 13C, engagement catheter 254 includes a vacuum channel 266 used for suction of a targeted tissue 268 in the heart and an injection channel 270 used for infusion of substances to targeted tissue 268, including, for example, a biological or non-biological degradable adhesive. As is shown in FIGS. 13B and 13C, injection channel 270 is ring-shaped, which tends to provide relatively even dispersal of the infused substance over the targeted tissue, but other shapes of injection channels may be suitable. A syringe 272 is attached to injection channel 270 for delivery of the appropriate substances to injection channel 270, and a syringe 274 is attached to vacuum channel 266 through a vacuum port (not shown) at the proximal end of engagement catheter 254 to provide appropriate suction through vacuum channel 266. At the distal end of engagement catheter 254, a suction port 278 is attached to vacuum channel 266 for contacting targeted tissue 268, such that suction port 278 surrounds targeted tissue 268, which is thereby encompassed within the circumference of suction port 278. Although syringe 274 is shown in FIG. 13B as the vacuum source providing suction for engagement catheter 254, other types of vacuum sources may be used, such as a controlled vacuum system providing specific suction pressures. Similarly, syringe 272 serves as the external fluid source in the embodiment shown in FIG. 13B, but other external fluid sources may be used.

A route of entry for use of various embodiments disclosed herein is through the jugular or femoral vein to the superior or inferior vena cavae, respectively, to the right atrial wall or atrial appendage (percutaneously) to the pericardial sac (through puncture).

Referring now to FIG. 12B, an engagement catheter 280 is placed via standard approach into the jugular or femoral vein. The catheter, which may be 4 or 5 Fr., is positioned under fluoroscopic or echocardiographic guidance into the right atrial appendage 282. Suction is initiated to aspirate a portion of atrial appendage 282 away from the pericardial sac 286 that surrounds the heart. As explained herein, aspiration of the heart tissue is evidenced when no blood can be pulled back through engagement catheter 280 and, if suction pressure is being measured, when the suction pressure gradually increases. A delivery catheter 290 is then inserted through a lumen of engagement catheter 280. A small perforation can be made in the aspirated atrial appendage 282 with a needle such as needle 260, as shown in FIGS. 12A and 13A. A guide wire (not shown) can then be advanced through delivery catheter 290 into the pericardial space to secure the point of entry 292 through the atrial appendage and guide further insertion of delivery catheter 290 or another catheter. Fluoroscopy or echocardiogram can be used to confirm the position of the catheter in the pericardial space. Alternatively, a pressure tip needle can sense the pressure and measure the pressure change from the atrium (about 10 mmHg) to the pericardial space (about 2 mmHg). This is particularly helpful for transeptal access where puncture of arterial structures (e.g., the aorta) can be diagnosed and sealed with an adhesive, as described in more detail below.

Although aspiration of the atrial wall or the atrial appendage retracts the wall or appendage from the pericardial sac to create additional pericardial space, $CO_2$ gas can be delivered through a catheter, such as delivery catheter 290, into the pericardial space to create additional space between the pericardial sac and the heart surface.

Figure 14B:
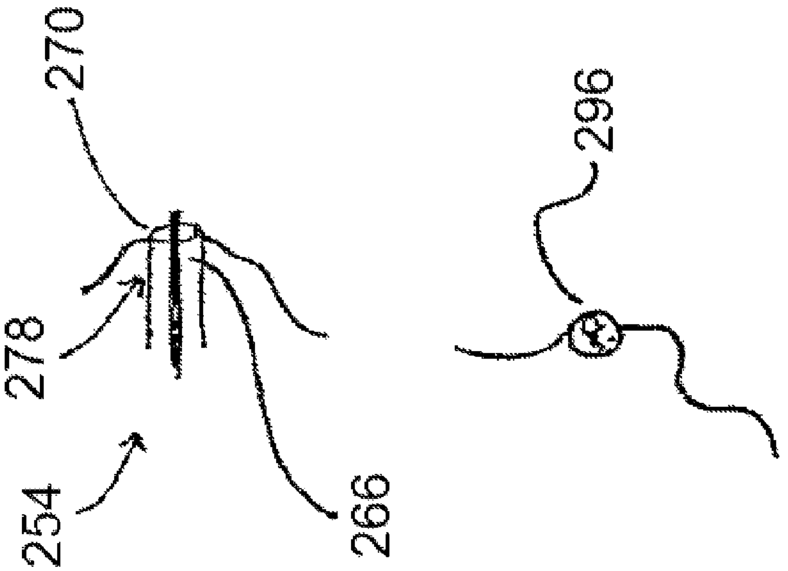
FIG. 14B shows the resealing of a puncture according to an embodiment as disclosed herein.
Figure 14A:
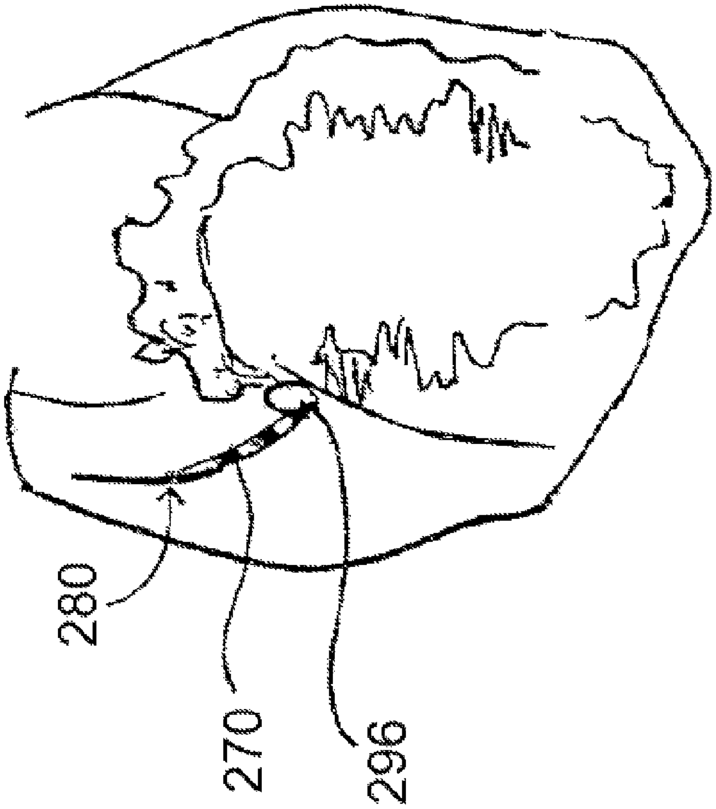
FIG. 14A shows removal of an embodiment of a catheter as disclosed herein.

Referring now to FIG. 14A, the catheter system shown in FIG. 12B is retrieved by pull back through the route of entry. However, the puncture of the targeted tissue in the heart (e.g., the right atrial appendage as shown in FIG. 14A) may be sealed upon withdrawal of the catheter, which prevents bleeding into the pericardial space. The retrieval of the catheter may be combined with a sealing of the tissue in one of several ways: (1) release of a tissue adhesive or polymer 296 via injection channel 270 to seal off the puncture hole, as shown in FIG. 14B; (2) release of an inner clip or mechanical stitch to close off the hole from the inside of the cavity; or (3) mechanical closure of the heart with a sandwich type mechanical device that approaches the hole from both sides of the wall (see FIGS. 15A, 15B, and 15C). In other words, closure may be accomplished by using, for example, a biodegradable adhesive material (e.g., fibrin glue or cyanomethacrylate), a magnetic system, or an umbrella-shaped nitinol stent. An example of the closure of a hole in the atrium is shown in FIG. 3B. Engagement catheter 254 is attached to targeted tissue 268 using suction through suction port 278. Tissue adhesive 296 is injected through injection channel 270 to coat and seal the puncture wound in targeted tissue 268. Engagement catheter 254 is then withdrawn, leaving a plug of tissue adhesive 296 attached to the atrial wall or atrial appendage.

Figure 15B:
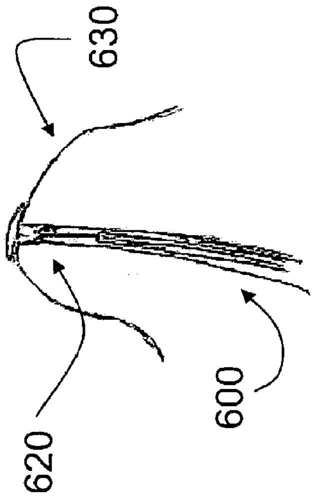
FIGS. 15A to 15C show a closure of a hole in the atrial wall using an embodiment as disclosed herein.
Figure 15C:
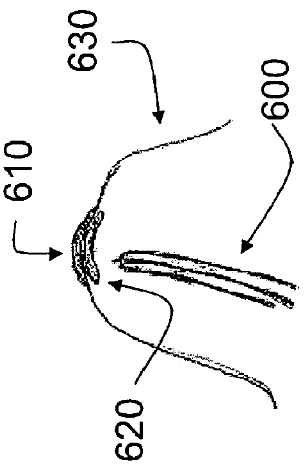
Figure 15A:
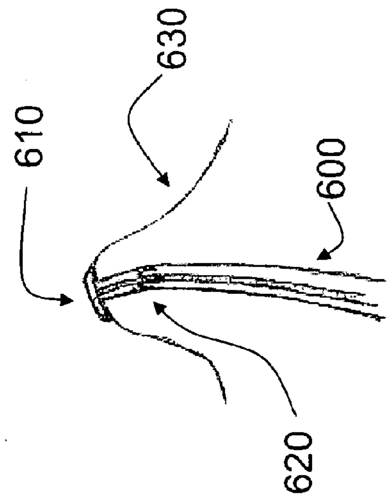

Another example for sealing the puncture wound in the atrial wall or appendage is shown in FIGS. 15A, 15B, and 15C. A sandwich-type closure member, having an external cover 610 and an internal cover 620, is inserted through the lumen of engagement catheter 600, which is attached to the targeted tissue of an atrial wall 630. Each of external and internal covers 610 and 620 is similar to an umbrella in that it can be inserted through a catheter in its folded configuration and expanded to an expanded configuration once it is outside of the catheter. As shown in FIG. 15A, external cover 610 is deployed (in its expanded configuration) on the outside of the atrial wall to seal a puncture wound in the targeted tissue, having already been delivered through the puncture wound into the pericardial space. Internal cover 620 is delivered through engagement catheter 600 (in its folded configuration), as shown in FIGS. 15A and 15B, by an elongated delivery wire 615, to which internal cover 620 is reversibly attached. Once internal cover 620 is in position on the inside of atrial wall 630 at the targeted tissue, internal cover 620 is deployed to help seal the puncture wound in the targeted tissue (see FIG. 15C). Engagement catheter 600 then releases its grip on the targeted tissue and is withdrawn, leaving the sandwich-type closure to seal the puncture wound, as shown in FIG. 15C. External cover 610 and internal cover 620 may be held in place using adhesion. Similarly, external cover 610 and internal cover 620 may be held in place using magnetic forces, such as, for example, by the inside face (not shown) of external cover 610 comprising a magnet, by the inside face (not shown) of internal cover 620 comprising a magnet, or both inside faces of external cover 610 or internal cover 620 comprising a magnet.

FIGS. 16A, 16B, 16C, and 16D show another embodiment of an engagement catheter as disclosed herein. Engagement catheter 700 is an elongated tube having a proximal end 710 and a distal end 720, as well as two lumens 730, 740 extending between proximal end 710 and distal end 720. Lumens 730, 740 are formed by concentric inner wall 750 and outer wall 760, as particularly shown in FIGS. 16B and 16C. At proximal end 710, engagement catheter 700 includes a vacuum port 770, which is attached to lumen 730 so that a vacuum source can be attached to vacuum port 770 to create suction in lumen 730, thereby forming a suction channel. At distal end 720 of catheter 700, a suction port 780 is attached to lumen 730 so that suction port 780 can be placed in contact with heart tissue 775 (see FIG. 16D) for aspirating the tissue, thereby forming a vacuum seal between suction port 780 and tissue 775 when the vacuum source is attached and engaged. The vacuum seal enables suction port 780 to grip, stabilize, and retract tissue 775. For example, attaching a suction port to an interior atrial wall using a vacuum source enables the suction port to retract the atrial wall from the pericardial sac surrounding the heart, which enlarges the pericardial space between the atrial wall and the pericardial sac.

Figures 16A, 16B, 16C:
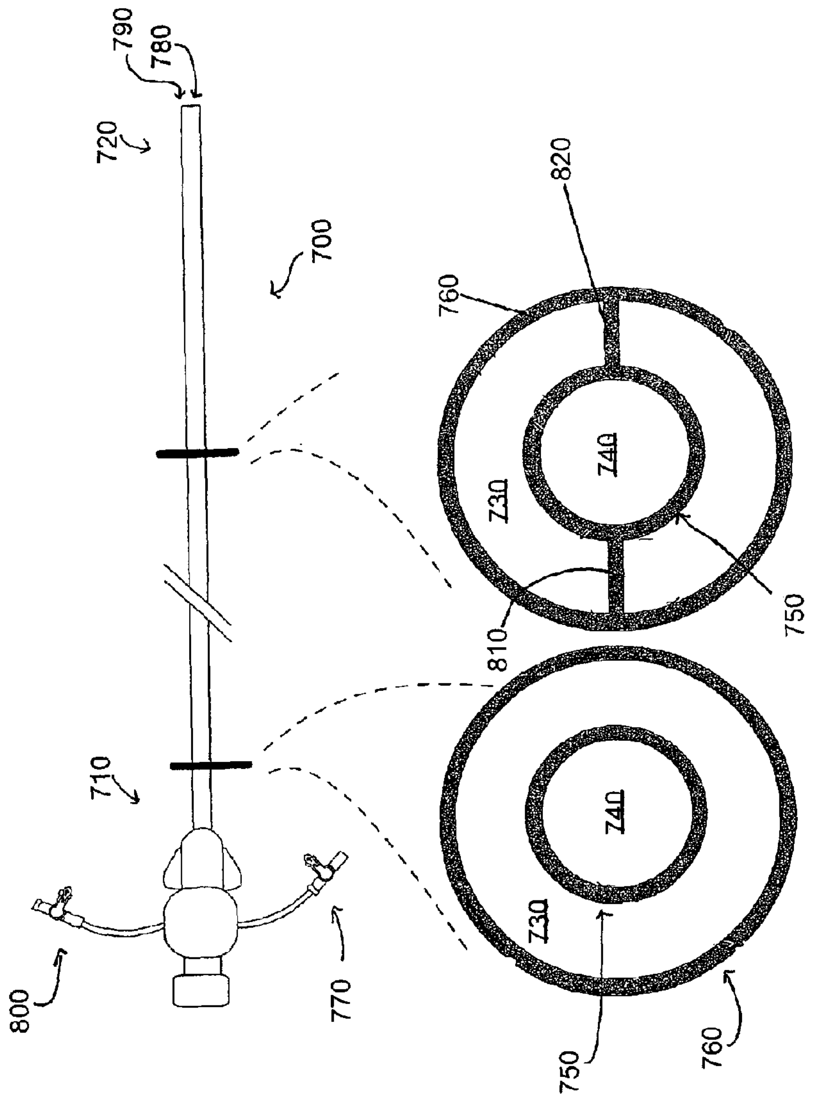
FIG. 16A shows an embodiment of an engagement catheter as disclosed herein.
FIG. 16B shows a cross-sectional view of the proximal end of the engagement catheter shown in FIG. 16A.
FIG. 16C shows a cross-sectional view of the distal end of the engagement catheter shown in FIG. 16A.

As shown in FIG. 16C, two internal lumen supports 810, 820 are located within lumen 730 and are attached to inner wall 750 and outer wall 760 to provide support to the walls. These lumen supports divide lumen 730 into two suction channels. Although internal lumen supports 810, 820 extend from distal end 720 of catheter 700 along a substantial portion of the length of catheter 700, internal lumen supports 810, 820 may or may not span the entire length of catheter 700. Indeed, as shown in FIGS. 16A, 16B, and 16C, internal lumen supports 810, 820 do not extend to proximal end 710 to ensure that the suction from the external vacuum source is distributed relatively evenly around the circumference of catheter 700. Although the embodiment shown in FIG. 16C includes two internal lumen supports, other embodiments may have just one internal support or even three or more such supports.

Figure 16D:
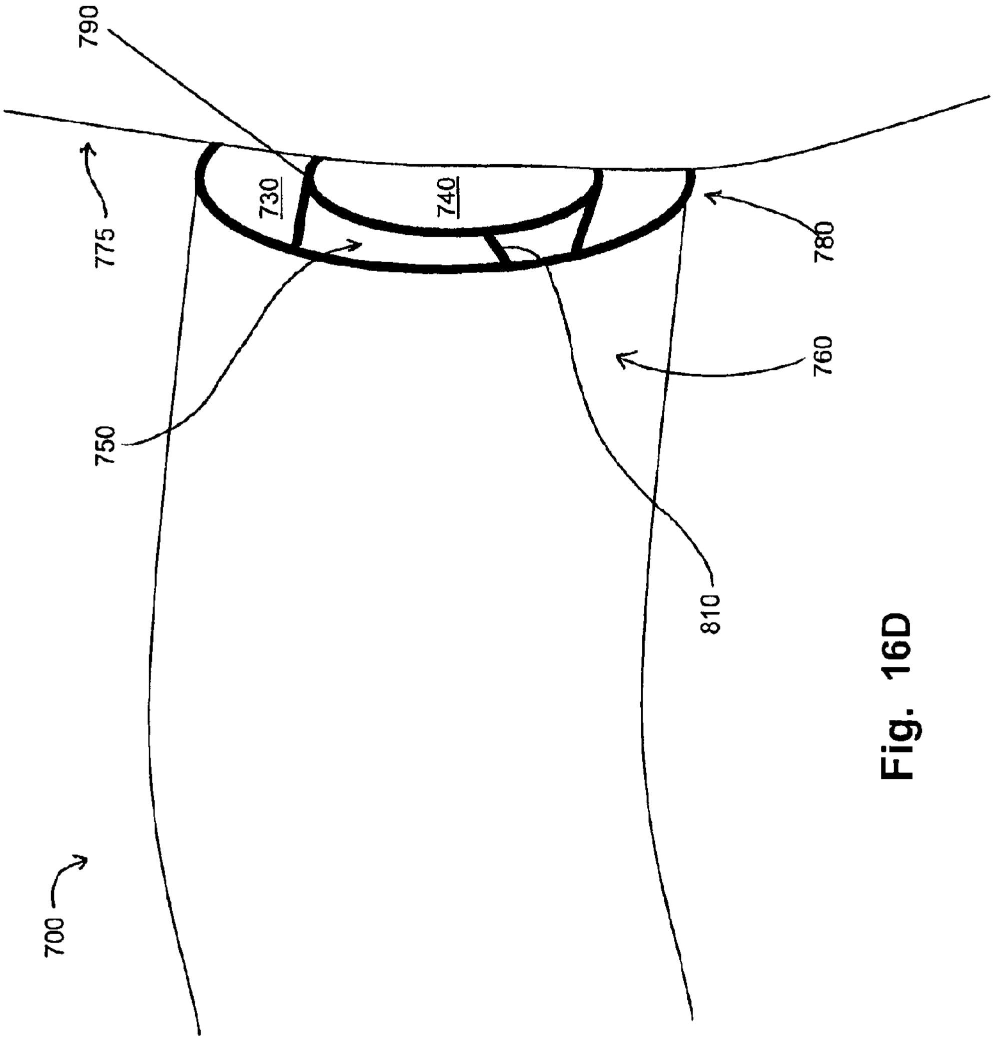
FIG. 16D shows the engagement catheter shown in FIG. 5A approaching a heart wall from inside of the heart.

FIG. 16D shows engagement catheter 700 approaching heart tissue 775 for attachment thereto. It is important for the clinician performing the procedure to know when the suction port has engaged the tissue of the atrial wall or the atrial appendage. For example, in reference to FIG. 16D, it is clear that suction port 780 has not fully engaged tissue 775 such that a seal is formed. However, because suction port 780 is not usually seen during the procedure, the clinician may determine when the proper vacuum seal between the atrial tissue and the suction port has been made by monitoring the amount of blood that is aspirated, by monitoring the suction pressure with a pressure sensor/regulator, or both. For example, as engagement catheter 700 approaches the atrial wall tissue (such as tissue 775) and is approximately in position, the suction can be activated through lumen 730. A certain level of suction (e.g., 10 mmHg) can be imposed and measured with a pressure sensor/regulator. As long as catheter 700 does not engage the wall, some blood will be aspirated into the catheter and the suction pressure will remain the same. However, when catheter 700 engages or attaches to the wall of the heart (depicted as tissue 775 in FIG. 16D), minimal blood is aspirated and the suction pressure will start to gradually increase. Each of these signs can alert the clinician (through alarm or other means) as an indication of engagement. The pressure regulator is then able to maintain the suction pressure at a preset value to prevent over-suction of the tissue.

An engagement catheter, such as engagement catheter 700, may be configured to deliver a fluid or other substance to tissue on the inside of a wall of the heart, including an atrial wall or a ventricle wall. For example, lumen 740 shown in FIGS. 16A and 16C includes an injection channel 790 at distal end 720. Injection channel 790 dispenses to the targeted tissue a substance flowing through lumen 740. As shown in FIG. 16D, injection channel 790 is the distal end of lumen 740. However, in other embodiments, the injection channel may be ring-shaped (see FIG. 13C) or have some other suitable configuration.

Substances that can be locally administered with an engagement catheter include preparations for gene or cell therapy, drugs, and adhesives that are safe for use in the heart. The proximal end of lumen 740 has a fluid port 800, which is capable of attachment to an external fluid source for supply of the fluid to be delivered to the targeted tissue. Indeed, after withdrawal of a needle from the targeted tissue, as discussed herein, an adhesive may be administered to the targeted tissue by the engagement catheter for sealing the puncture wound left by the needle withdrawn from the targeted tissue.

Figures 17A, 17B, 17C:
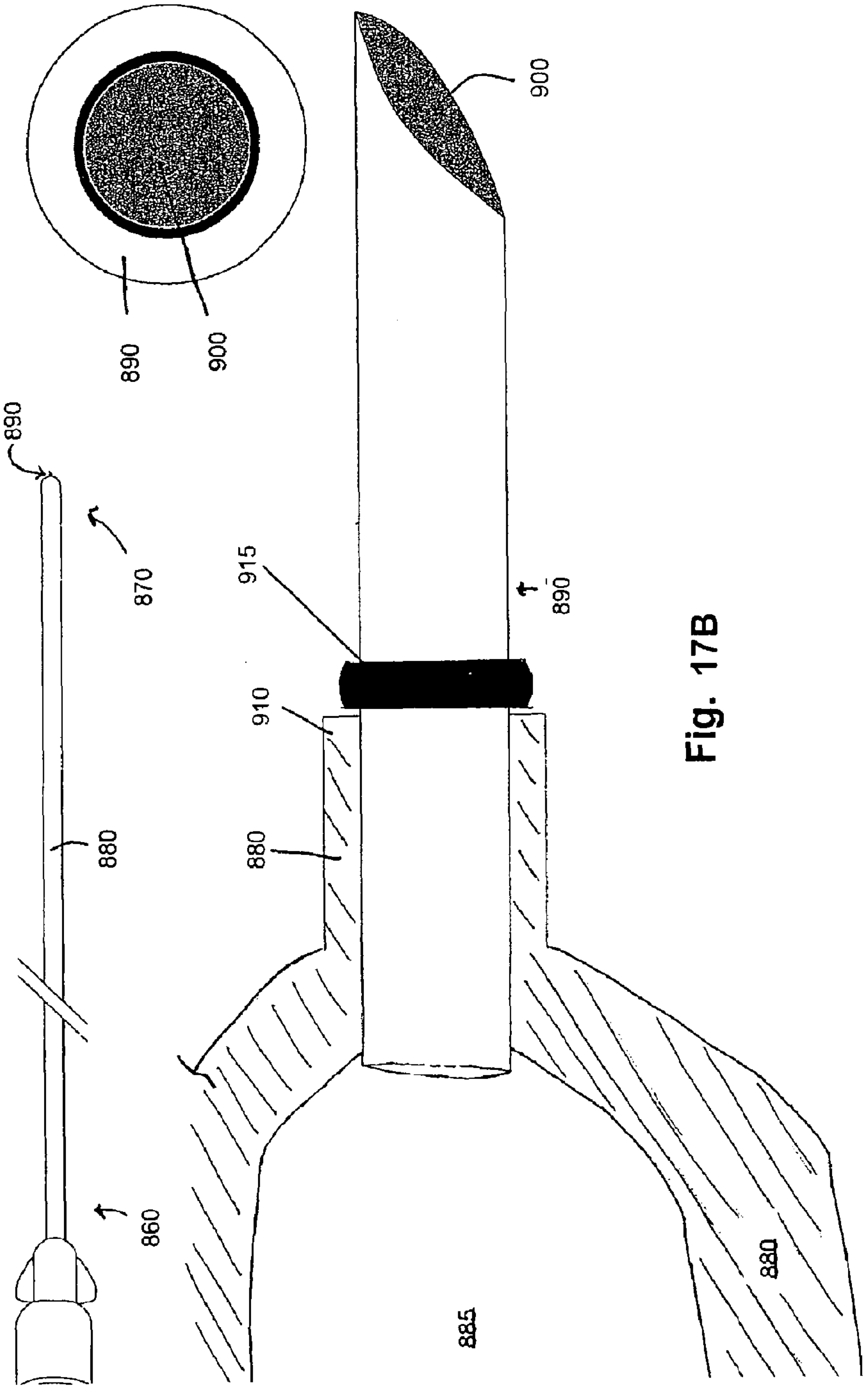
FIG. 17A shows an embodiment of a delivery catheter as disclosed herein.
FIG. 17B shows a close-up view of the needle shown in FIG. 6A.
FIG. 17C shows a cross-sectional view of the needle shown in FIGS. 6A and 6B.

Referring now to FIGS. 17A, 17B, and 17C, there is shown a delivery catheter 850 comprising an elongated hollow tube 880 having a proximal end 860, a distal end 870, and a lumen 885 along the length of the catheter. Extending from distal end 870 is a hollow needle 890 in communication with lumen 885. Needle 890 is attached to distal end 870 in the embodiment of FIGS. 17A, 17B, and 17C, but, in other embodiments, the needle may be removably attached to, or otherwise located at, the distal end of the catheter (see FIG. 12A). In the embodiment shown in FIGS. 17A, 17B, and 17C, as in certain other embodiments having an attached needle, the junction (i.e., site of attachment) between hollow tube 880 and needle 890 forms a security notch 910 circumferentially around needle 890 to prevent needle 890 from over-perforation. Thus, when a clinician inserts needle 890 through an atrial wall to gain access to the pericardial space, the clinician will not, under normal conditions, unintentionally perforate the pericardial sac with needle 890 because the larger diameter of hollow tube 880 (as compared to that of needle 890) at security notch 910 hinders further needle insertion. Although security notch 910 is formed by the junction of hollow tube 880 and needle 890 in the embodiment shown in FIGS. 17A, 17B, and 17C, other embodiments may have a security notch that is configured differently. For example, a security notch may include a band, ring, or similar device that is attached to the needle a suitable distance from the tip of the needle. Like security notch 910, other security notch embodiments hinder insertion of the needle past the notch itself by presenting a larger profile than the profile of the needle such that the notch does not easily enter the hole in the tissue caused by entry of the needle.

It is useful for the clinician performing the procedure to know when the needle has punctured the atrial tissue. This can be done in several ways. For example, the delivery catheter can be connected to a pressure transducer to measure pressure at the tip of the needle. Because the pressure is lower and much less pulsatile in the pericardial space than in the atrium, the clinician can recognize immediately when the needle passes through the atrial tissue into the pericardial space.

Alternatively, as shown in FIG. 17B, needle 890 may be connected to a strain gauge 915 as part of the catheter assembly. When needle 890 contacts tissue (not shown), needle 890 will be deformed. The deformation will be transmitted to strain gauge 915 and an electrical signal will reflect the deformation (through a classical wheatstone bridge), thereby alerting the clinician. Such confirmation of the puncture of the wall can prevent over-puncture and can provide additional control of the procedure.

In some embodiments, a delivery catheter, such as catheter 850 shown in FIGS. 17A, 17B, and 17C, is used with an engagement catheter, such as catheter 700 shown in FIGS. 16A, 16B, 16C, and 16D, to gain access to the pericardial space between the heart wall and the pericardial sac. For example, engagement catheter 700 may be inserted into the vascular system and advanced such that the distal end of the engagement catheter is within the atrium. The engagement catheter may be attached to the targeted tissue on the interior of a wall of the atrium using a suction port as disclosed herein. A standard guide wire may be inserted through the lumen of the delivery catheter as the delivery catheter is inserted through the inner lumen of the engagement catheter, such as lumen 740 shown in FIGS. 16B and 16C. Use of the guide wire enables more effective navigation of the delivery catheter 850 and prevents the needle 890 from damaging the inner wall 750 of the engagement catheter 700. When the tip of the delivery catheter with the protruding guide wire reaches the atrium, the wire is pulled back, and the needle is pushed forward to perforate the targeted tissue. The guide wire is then advanced through the perforation into the pericardial space, providing access to the pericardial space through the atrial wall.

Referring again to FIGS. 17A, 17B, and 17C, lumen 885 of delivery catheter 850 may be used for delivering fluid into the pericardial space after needle 890 is inserted through the atrial wall or the atrial appendage. After puncture of the wall or appendage, a guide wire (not shown) may be inserted through needle lumen 900 into the pericardial space to maintain access through the atrial wall or appendage. Fluid may then be introduced to the pericardial space in a number of ways. For example, after the needle punctures the atrial wall or appendage, the needle is generally withdrawn. If the needle is permanently attached to the delivery catheter, as in the embodiment shown in FIGS. 17A and 17B, then delivery catheter 850 would be withdrawn and another delivery catheter (without an attached needle) would be introduced over the guide wire into the pericardial space. Fluid may then be introduced into the pericardial space through the lumen of the second delivery catheter.

In some embodiments, however, only a single delivery catheter is used. In such embodiments, the needle is not attached to the delivery catheter, but instead may be a needle wire (see FIG. 12A). In such embodiments, the needle is withdrawn through the lumen of the delivery catheter, and the delivery catheter may be inserted over the guide wire into the pericardial space. Fluid is then introduced into the pericardial space through the lumen of the delivery catheter.

The various embodiments disclosed herein may be used by clinicians, for example: (1) to deliver genes, cells, drugs, etc.; (2) to provide catheter access for epicardial stimulation; (3) to evacuate fluids acutely (e.g., in cases of pericardial tamponade) or chronically (e.g., to alleviate effusion caused by chronic renal disease, cancer, etc.); (4) to perform transeptal puncture and delivery of a catheter through the left atrial appendage for electrophysiological therapy, biopsy, etc.; (5) to deliver a magnetic glue or ring through the right atrial appendage to the aortic root to hold a percutaneous aortic valve in place; (6) to deliver a catheter for tissue ablation, e.g., to the pulmonary veins, or right atrial and epicardial surface of the heart for atrial and ventricular arrythmias; (7) to deliver and place epicardial, right atrial, and right and left ventricle pacing leads (as discussed herein); (8) to occlude the left atrial appendage through percutaneous approach; and (9) to visualize the pericardial space with endo-camera or scope to navigate the epicardial surface of the heart for therapeutic delivery, diagnosis, lead placement, mapping, etc. Many other applications, not explicitly listed here, are also possible and within the scope of the present disclosure.

Figure 18:
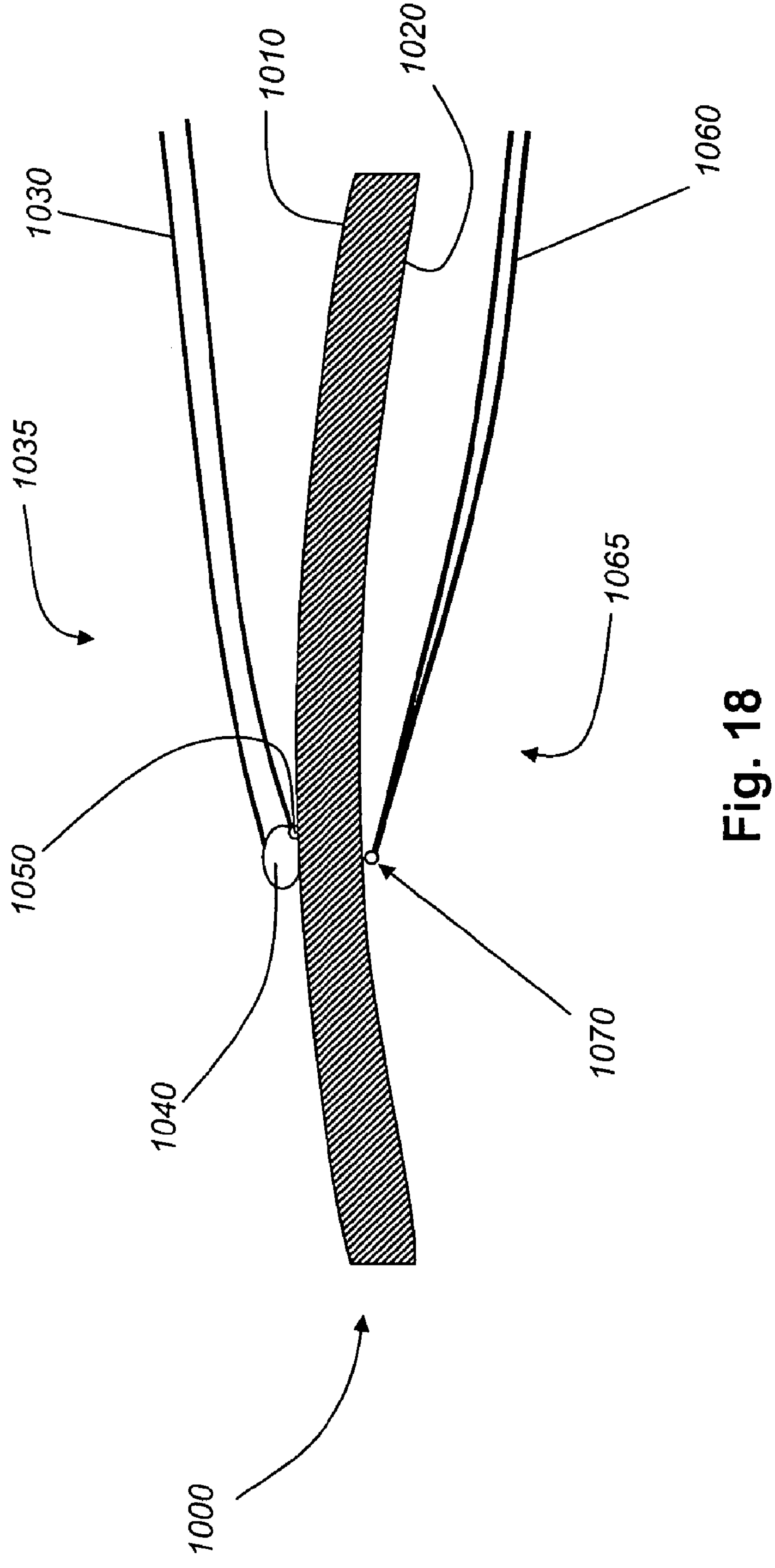
FIG. 18 shows a side view of an embodiment of an external catheter and an embodiment of an internal catheter as disclosed herein.

Referring now to FIG. 18, there is shown a cardiac tissue 1000 having a first surface 1010 and an opposing surface 1020. First surface 1010 comprises an epicardial surface of the heart, while opposing surface 1020 comprises an endocardial surface of the heart. An external catheter 1030 is shown being used in conjunction with an internal catheter 1060 to perform ablation on the epicardial surface of the heart. External catheter 1030 comprises a distal end 1035, a first magnet 1040 positioned at distal end 1035 of external catheter 1030, and an ablation contact 1050 positioned at distal end 1035 of external catheter 1030. Ablation contact 1050 is configured to remove or destroy tissue by contacting the tissue and emitting radiofrequency energy into the tissue. However, other embodiments of ablation contacts may destroy tissue using electrical energy, intense cold (cryoablation), or any other suitable method.

Internal catheter 1060 comprises a distal end 1065 and a first magnet 1070 positioned at distal end 1065 of internal catheter 1060. First magnet 1070 comprises a traditional magnet, also known as a permanent magnet or ferromagnet. As shown in FIG. 18, first magnet 1070 is sphere-like in shape, but other embodiments of magnets may be of other suitable shapes. In addition, unlike the embodiment of FIG. 18, at least some embodiments of magnets comprise, instead of a permanent magnet, an electrode that is capable of acting as an electromagnet. Such electrodes are capable of transitioning between a magnetized state, in which the electrode emits a magnetic field capable of attracting other magnets, and a nonmagnetized state, in which the electrode does not emit any significant magnetic field. Such electrodes are connected to a power source and can be transitioned to the magnetized state or to the nonmagnetized state by switching the power on and off, respectively, or by any other method.

In the embodiment shown in FIG. 18, first magnet 1040 of external catheter 1030 comprises a permanent magnet. However, at least some other embodiments of the first magnet of the external catheter may comprise an electrode rather than a permanent magnet. Such electrodes act as electromagnets. Thus, for example, where the first magnet of the external catheter comprises a first electrode, the first electrode is capable of transitioning between a magnetized state, in which the electrode attracts the first magnet of the internal catheter, and a nonmagnetized state, in which the electrode does not significantly attract the first magnet of the internal catheter. This transition between the magnetized and nonmagnetized states may be accomplished by supplying and removing electric current to the electrode.

As shown in FIG. 18, portions of external catheter 1030, specifically ablation contact 1050 and first magnet 1040 of external catheter 1030, are positioned on first surface 1010 of tissue 1000. A portion of internal catheter 1060, specifically first magnet 1070 of internal catheter 1060, is positioned on opposing surface 1020 of tissue 1000. Internal catheter 1060 is configured for engaging external catheter 1030 in this position such that the clinician's manipulation of internal catheter 1060 can direct external catheter 1030. Specifically, in the embodiment shown in FIG. 18, the magnetic field emitted by first magnet 1070 of internal catheter 1060 engages first magnet 1040 of external catheter 1030, thereby attracting first magnet 1040 of external catheter 1030 such that distal end 1035 of external catheter 1030 is pulled along first surface 1010 toward the position of first magnet 1070 of internal catheter 1060. Thus, as the clinician moves distal end 1065 of internal catheter 1060 along opposing surface 1020, distal end 1035 of external catheter 1030 is directed toward a desired location on first surface 1010.

While the embodiment of FIG. 18 includes an external catheter having only one magnet, at least some other embodiments of external catheters have a plurality of magnets, such as a second magnet comprising a second electrode. Indeed, other embodiments of external catheter may have a third electrode, or even more electrodes. Each such electrode is positioned at or near the distal end of the external catheter, and each is capable of transitioning between a magnetized state, in which it attracts a magnet of the internal catheter, and a nonmagnetized state, in which the electrode does not significantly attract the magnet of the internal catheter.

Figure 19:
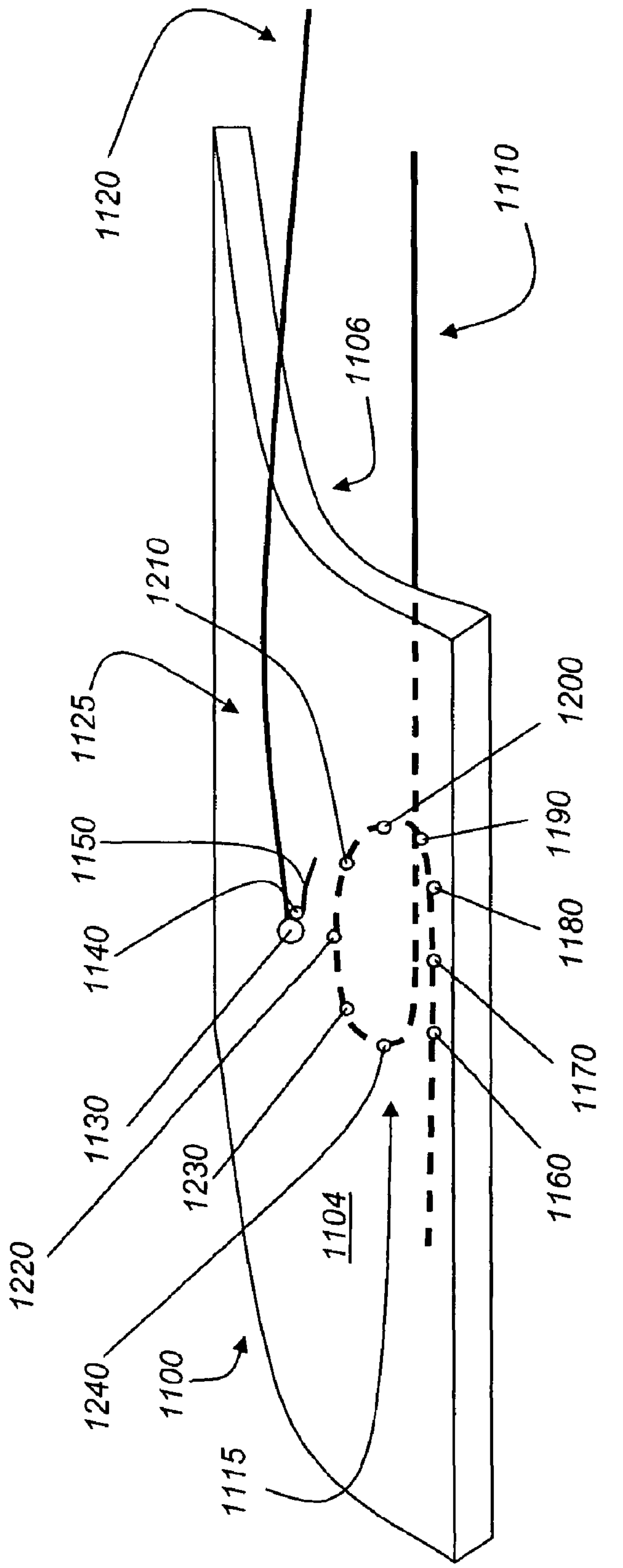
FIG. 19 shows a perspective view of another embodiment of an external catheter and another embodiment of an internal catheter as disclosed herein.

Likewise, at least some other embodiments of internal catheters may have a plurality of magnets. For example, FIG. 19 shows an internal catheter 1110 having multiple magnets. Tissue 1100 has a first surface 1104, which is an epicardial surface of a heart, and an opposing surface 1106, which is an endocardial surface of the heart. An external catheter 1120 comprises a first magnet 1130 and an ablation contact 1140, each of which is positioned at distal end 1125 of external catheter 1120. As shown in FIG. 19, ablation contact 1140 is in contact with surface 1104. The path of the movement of ablation contact 1140 on surface 1104 is indicated by scarring 1150, which is the ablated tissue.

As noted, internal catheter 1110 includes a plurality of magnets. A first magnet 1160 comprises a first electrode capable of transitioning between a magnetized state, in which the electrode attracts first magnet 1130 of external catheter 1120, and a nonmagnetized state, in which the electrode does not significantly attract first magnet 1130 of external catheter 1120. First magnet 1160 of internal catheter 1110 does not significantly attract first magnet 1130 of external catheter 1120 if external catheter 1120 cannot be moved by manipulation of internal catheter 1110. Internal catheter further comprises a second magnet comprising a second electrode 1170, a third magnet comprising a third electrode 1180, a fourth magnet comprising a fourth electrode 1190, a fifth magnet comprising a fifth electrode 1200, a sixth magnet comprising a sixth electrode 1210, a seventh magnet comprising a seventh electrode 1220, an eighth magnet comprising an eighth electrode 1230, and a ninth magnet comprising a ninth electrode 1240. Each electrode acts as an electromagnet and is capable of transitioning between a magnetized state, in which the electrode attracts first magnet 1130 of external catheter 1120, and a nonmagnetized state, in which the electrode does not significantly attract first magnet 1130 of external catheter 1120. Each electrode is positioned at distal end 1115 of internal catheter 1110. However, at least some electrodes of at least some other embodiments may be positioned on the internal catheter near the distal end of the internal catheter, so long as each of the electrodes can be inserted into the patient's heart (or other body lumen of interest) adjacent to the tissue to be ablated or otherwise treated.

As shown, internal catheter 1110 forms a loop within the heart (i.e., on the endocardial side of the cardiac tissue) such that each electrode is located within the heart. In at least some embodiments, the loop may be formed in the catheter within the heart.

Although internal catheter 1110 comprises nine electrodes, other embodiments of internal catheters may have almost any number of electrodes (for example, from one electrode to twelve electrodes or more), depending on the intended use of the internal catheter.

Various embodiments of internal and external catheters may be used with an engagement catheter, as disclosed herein. In such embodiments, the external catheter, and optionally the internal catheter, would be configured for at least partial insertion into the second lumen of the engagement catheter (see, e.g., FIG. 13A). Any internal or external catheters to be delivered to the relevant treatment site through the engagement catheter must be sized and shaped to fit within the engagement catheter lumen.

However, depending on the location of the tissue targeted for ablation, the internal catheter may need to access locations on the endocardial surface of the heart that are inaccessible from within the engagement catheter. In such cases, the internal catheter may be placed in the heart without use of the engagement catheter. Thus, to place the internal catheter at the proper location within the heart, clinicians may use radiography to visualize the catheter and the cardiac anatomy, or various other localization techniques may be used.

For example, a clinician may direct the placement of the internal catheter using data collected with an impedance catheter, as discussed herein.

Figure 20:
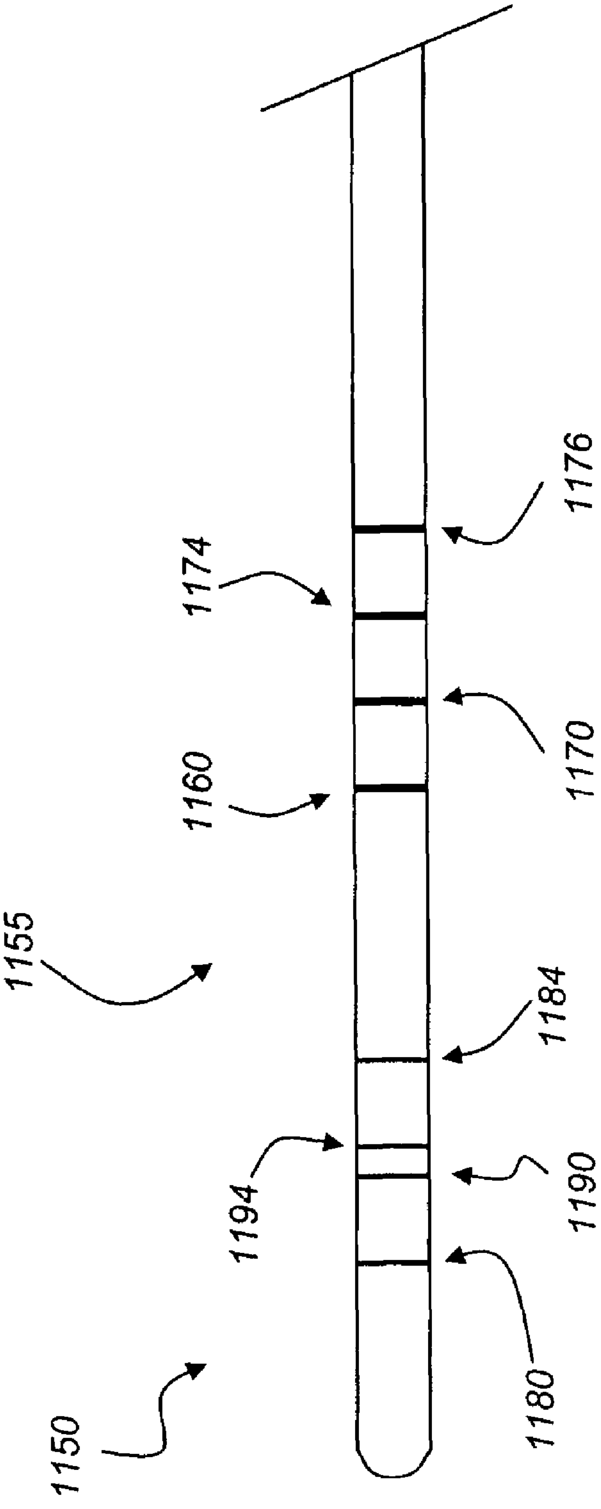
FIG. 20 shows a close-up view of a distal end of an embodiment of an internal catheter as disclosed herein.

Referring now to FIG. 20, there is shown distal end 1155 of an internal catheter 1150 comprising a first electrode 1160 positioned at distal end 1155, a second electrode 1170 positioned at distal end 1155, a third electrode 1174 positioned at distal end 1155, a fourth electrode 1176 positioned at distal end 1155, a pair of excitation electrodes 1180 and 1184 positioned at distal end 1155, and a pair of detection electrodes 1190 and 1194 positioned on internal catheter 1150 between excitation electrodes 1180 and 1184. Using the pair of excitation electrodes and the pair of detection electrodes, the anatomical structure of the inside of the heart can be determined, as disclosed herein, leading to more accurate placement of internal catheter 1150 prior to ablation. After internal catheter 1150 is correctly placed, electrodes 1160, 1170, 1174, and 1176 are used to engage an external catheter and direct an ablation contact on the external catheter across the epicardial surface of the heart, as discussed herein.

Using the catheter embodiments disclosed herein, a clinician can navigate an ablation catheter into the pericardial space, and therefore can ablate the epicardial surface of the heart, by engaging the ablation catheter with an internal catheter inside the heart. The pericardial space can be accessed using an engagement catheter, such as, for example, engagement catheter 700 shown in FIGS. 16A, 16B, 16C, and 16D. In addition, the internal catheter may be navigated within the blood vessels and heart, as disclosed herein.

For example, an external catheter (such as external catheter 1120 of FIG. 19), an internal catheter (such as internal catheter 1110 of FIG. 19), and an engagement catheter (such as engagement catheter 700 of FIG. 16A) are provided. Engagement catheter 700 is inserted into the heart and suction is initiated to aspirate the cardiac tissue from the surrounding pericardial sac (see, e.g., FIG. 13B). A perforation of the tissue is made, for example, with a needle advanced through one of the lumens (e.g., lumen 740) of engagement catheter 700, and a guide wire is inserted through the hole in the cardiac tissue into the pericardial space, thereby providing access to the pericardial space. Distal end 1125 of external catheter 1120 (shown in FIG. 19), is guided into the pericardial space and is placed adjacent to the epicardial surface of the heart. Distal end 1115 of internal catheter 1110 is guided into the interior of the heart and placed adjacent to an opposing surface of the heart (i.e., the endocardial surface of the heart).

Internal catheter 1110 is manipulated to direct ablation contact 1140 of external catheter 1120 to contact a first targeted location on the epicardial surface of the heart. When the ablation contact is activated, ablation of the first targeted location occurs.

Manipulation of the internal catheter to direct the ablation contact can occur in a number of ways. For example, referring to FIG. 18, by bringing magnet 1070 of internal catheter 1060 into sufficient proximity to magnet 1040 of external catheter 1030, magnet 1070 of internal catheter 1060 engages magnet 1040 of external catheter 1030 (if both magnets are activated). Internal catheter 1060 can then be moved along the endocardial surface 1020 of cardiac tissue 1000 and, because of the magnetic engagement between the internal and external catheters, ablation contact 1050 of external catheter 1030 will move along the epicardial surface 1010 of cardiac tissue 1000. In other words, the ablation contact will follow essentially the same path along the epicardial surface that the magnet of the internal catheter follows along the endocardial surface of the heart. This technique can be used to place the ablation contact on the precise location of the epicardial surface targeted for ablation. In such a case, the ablation contact is activated only when it is properly positioned; it may then be deactivated after ablation is complete. However, the ablation contact may remain activated while the external catheter is moved to a second targeted location on the epicardial surface of the heart. In this case, the tissue is ablated not only at the first and second targeted locations, but also along the path the ablation contact took when it moved from the first targeted location to the second targeted location.

An internal catheter having a multiplicity of magnets comprising electrodes may be manipulated to direct the ablation contact in other ways. For example, when using a catheter with a multiplicity of electrodes, such as internal catheter 1110 shown in FIG. 19, the clinician may not need to move the internal catheter after the ablation contact of the external catheter is placed at the first targeted location on the epicardial surface of the heart. After the ablation contact is directed to the first targeted location and ablation is accomplished at the first targeted location, the ablation contact may be directed solely by manipulation of the electrodes on the internal catheter. For example, referring to FIG. 19, ablation contact 1140 may be directed across surface 1104 by activating and deactivating the electrodes on internal catheter 1110. If magnet 1130 of external catheter 1120 is engaged by first electrode 1160, then first electrode 1160 is deactivated by switching first electrode 1160 to the nonmagnetized state. Second electrode 1170 is then activated by switching second electrode 1170 to the magnetized state, thereby attracting first magnet 1130 of external catheter 1120 (and therefore ablation contact 1140) to the second targeted location on surface 1140. If ablation contact 1140 is active during the movement of the external catheter, then the tissue between the first targeted location and the second targeted location will be ablated (see, e.g., scarring 1150). After ablation contact 1140 reaches the second targeted location, second electrode 1170 is switched to the nonmagnetized state and third electrode 1180 is switched to the magnetized state, moving ablation contact 1140 to the third targeted location. This process is then repeated through the desired number of electrodes until the ablation is complete.

Where the internal catheter is sufficiently flexible, the catheter may be positioned in a loop within the heart such that the electrodes form a circumference (see, e.g., FIG. 19). Alternatively, a loop may be preformed in the catheter and delivered to the inside of the heart. Regardless, the circumference predefines the region to be ablated. The ablation contact of the external catheter is directed by the sequential activation and deactivation of electrodes, as described above, such that the path of ablation follows the circumference formed by the electrodes. In other words, once ablation is completed at one location, the magnetic field is turned off at that point and turned on at the adjacent point, thereby moving the external catheter (and therefore the ablation contact) into a new position along the circumference. This method of ablation may be especially useful for ablating around a pulmonary vein (i.e., at the pulmonary vein-atrial junction).

Certain of the disclosed embodiments have been shown having an external catheter with an ablation contact and an internal catheter that is used to direct the external catheter. However, at least some other embodiments have an ablation contact on an internal catheter that is directed by manipulation of the external catheter.

While various embodiments of devices, systems and methods for navigating a catheter along the epicardial surface of the heart have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system for navigating an elongated body on a surface of a tissue, comprising:

an internal elongated body comprising a distal end and a first element positioned at or near the distal end of the internal elongated body, the internal elongated body devoid of an ablation contact; and an external elongated body comprising a distal end and a second element and an ablation contact positioned at or near the distal end of the external elongated body, the ablation contact being configured to remove or destroy tissue, wherein the first element and the second element are magnetically attracted to each other;

wherein when a portion of the external elongated body is positioned on or adjacent to a first surface of a tissue and when a portion of the internal elongated body is positioned on or adjacent to an opposing surface of the tissue, manipulation of the internal elongated body directs movement of the external elongated body to a first location to facilitate removal or destruction of tissue at the first surface at a first location; and wherein the external elongated body is further operable to remove or destroy tissue at the first surface at a second location directed by the internal elongated body without moving the internal elongated body.

2. The system of claim 1, wherein at least one of the first element and/or the second element comprises a magnet, and wherein the other of the first element and/or the second element comprises a magnetically-attractive non-magnet material if the first element and the second element do not both comprise magnets, and wherein the internal elongated body and the external elongated body are each selected from the group consisting of a catheter and a wire.

3. The system of claim 1, wherein the external elongated body is further operable to destroy or remove tissue along the first surface between the first location and the second location without moving the internal elongated body.

4. The system of claim 1, wherein the first element of the internal elongated body comprises a first electrode capable of transitioning between a magnetized state, in which the first electrode attracts the second element of the external elongated body, and a nonmagnetized state, in which the first electrode does not significantly attract the second element of the external elongated body.

5. The system of claim 4, wherein the internal elongated body further comprises a second electrode positioned at or near the distal end of the internal elongated body, the second electrode of the internal elongated body being capable of transitioning between a magnetized state, in which the second electrode attracts the second element of the external elongated body, and a nonmagnetized state, in which the second electrode does not significantly attract the second element of the external elongated body.

6. The system of claim 5, wherein the internal elongated body further comprises a third electrode, the third electrode is positioned at or near the distal end of the internal elongated body and the third electrode is capable of transitioning between a magnetized state, in which the third electrode attracts the second element of the external elongated body, and a nonmagnetized state, in which the third electrode does not significantly attract the second element of the external elongated body, and wherein the internal elongated body is capable of forming a loop within a heart such that the first, second, and third electrodes are located within the heart.

7. The system of claim 6, wherein the internal elongated body further comprises a fourth electrode, the fourth electrode is positioned at or near the distal end of the internal elongated body, the fourth electrode is capable of transitioning between a magnetized state, in which the fourth electrode attracts the second element of the external elongated body, and a nonmagnetized state, in which the fourth electrode does not significantly attract the second element of the external elongated body, and wherein the internal elongated body is capable of forming a loop within the heart such that the first, second, third, and fourth electrodes are located within the heart.

8. The system of claim 1, wherein the internal elongated body further comprises a pair of excitation electrodes positioned at or near the distal end of the internal elongated body and a pair of detection electrodes positioned on the internal elongated body between the pair of the excitation electrodes, the pair of excitation electrodes and the pair of detection electrodes connected to a processor capable of collecting conductance data and further capable of determining a profile of a body lumen based upon conductance data obtained using the pair of detection electrodes in connection with at least one fluid injection.

9. The system of claim 8, wherein the internal elongated body further comprises a passageway for passing a fluid through the internal elongated body to the body lumen, and wherein the conductance data is determined at each of a plurality of locations.

10. The system of claim 9, wherein the conductance data comprises a first conductance value determined at each of the plurality of locations when the pair of excitation electrodes and the pair of detection electrodes are immersed in a first fluid with a first conductivity and a second conductance value determined at each of the plurality of locations when the pair of excitation electrodes and the pair of detection electrodes are immersed in a second fluid with a second conductivity, wherein the first conductivity does not equal the second conductivity.

11. The system of claim 1, wherein the second element of the external elongated body comprises an external elongated body magnet comprising a first electrode capable of transitioning between a magnetized state, in which the first electrode attracts the first element of the internal elongated body, and a nonmagnetized state, in which the first electrode does not significantly attract the first element of the internal elongated body.

12. The system of claim 11, wherein the external elongated body further comprises a second electrode positioned at or near the distal end of the external elongated body, the second electrode of the external elongated body being capable of transitioning between a magnetized state, in which the second electrode attracts the first element of the internal elongated body, and a nonmagnetized state, in which the second electrode does not significantly attract the first element of the internal elongated body.

13. The system of claim 1, wherein the external elongated body further comprises a third element positioned at or near the distal end of the external elongated body, the third element selected from the group consisting of a second external elongated body magnet and a magnetically-attractive non-magnet material.

14. The system of claim 1, further comprising:

an engagement elongated body comprising a proximal end, a distal end, a first lumen extending between the proximal end and the distal end, a vacuum port located at or near the proximal end of the engagement elongated body in communication with the first lumen of the engagement elongated body and capable of operative connection to a vacuum source, and a suction port located at or near the distal end of the engagement elongated body and configured to removably attach to a targeted tissue on the interior of a wall of a heart and capable of forming a reversible seal with the targeted tissue when the vacuum source is operatively attached to the vacuum port; and wherein the external elongated body is configured for at least partial insertion into the first lumen of the engagement elongated body.

15. A system for navigating an elongated body on a surface of a tissue, comprising:

an internal elongated body comprising a distal end and a first element positioned at or near the distal end of the internal elongated body, the internal elongated body devoid of an ablation contact; and an external elongated body comprising a distal end and a second element and an ablation contact positioned at or near the distal end of the external elongated body, the ablation contact being configured to remove or destroy tissue, wherein the first element and the second element are magnetically attracted to each other;

wherein at least one of the first element and/or the second element comprises a magnet, and wherein the other of the first element and/or the second element comprises a magnetically-attractive non-magnet material if the first element and the second element do not both comprise magnets;

wherein the internal elongated body and the external elongated body are each selected from the group consisting of a catheter and a wire;

wherein when a portion of the external elongated body is positioned on or adjacent to a first surface of a tissue and when a portion of the internal elongated body is positioned on or adjacent to an opposing surface of the tissue, manipulation of the internal elongated body directs movement of the external elongated body to a first location to facilitate removal or destruction of tissue at the first surface at a first location; and wherein the external elongated body is further operable to remove or destroy tissue at the first surface at a second location and along the first surface between the first location and the second location directed by the internal elongated body without moving the internal elongated body.

16. A method of ablating a tissue, the method comprising the steps of:

positioning at least a portion of an internal elongated body adjacent to a first surface of a tissue, the internal elongated body comprising a distal end and a first element positioned at or near the distal end of the internal elongated body, the internal elongated body devoid of an ablation contact;

positioning at least a portion of an external elongated body adjacent to an opposing surface of the tissue, the external elongated body comprising a distal end and a second element and an ablation contact positioned at or near the distal end of the external elongated body, the ablation contact being configured to remove or destroy tissue, wherein the first element and the second element are magnetically attracted to each other;

manipulating the internal elongated body to direct the ablation contact of the external elongated body to a first location on the first surface of the tissue;

first ablating the first location on the first surface of the tissue using the external elongated body; and second ablating a second location on the first surface of the tissue using the external elongated body directed by the internal elongated body without moving the internal elongated body.

17. The method of claim 16, wherein the step of second ablating further comprises ablating along the first surface between the first location and the second location.

18. The method of claim 16, wherein the first surface of the tissue comprises an endocardial surface of a cardiac tissue, and wherein the opposing surface of the tissue comprises an epicardial surface of the cardiac tissue.

19. The method of claim 18, wherein:

the step of manipulating the internal elongated body comprises (i) engaging the first element of the internal elongated body with the second element of the external elongated body such that moving the first element of the internal elongated body moves the second element of the external elongated body, and (ii) moving the first element of the internal elongated body along the endocardial surface of the cardiac tissue such that the ablation contact of the external elongated body moves along the epicardial surface of the cardiac tissue to the first location on the epicardial surface of the cardiac tissue.

20. The method of claim 16, wherein the internal elongated body comprises a plurality electrodes positioned at or near the distal end of the internal elongated body, wherein the internal elongated body forms a loop within a heart, such that each of the plurality of electrodes are located within the heart, and wherein the method further comprises the step of:

ablating the first surface of the tissue in a specified circumference, the circumference being approximately defined by the loop of the internal elongated body.

* * * * *